US006995360B2

(12) United States Patent
Jones et al.

(10) Patent No.: US 6,995,360 B2
(45) Date of Patent: Feb. 7, 2006

(54) METHOD AND SENSOR FOR MONITORING GAS IN A DOWNHOLE ENVIRONMENT

(75) Inventors: Timothy Gareth John Jones, Cottenham (GB); Boris Matveev, St. Petersburg (RU); Vladimir Vaynshteyn, Southampton (GB); Christian Besson, Moscow (RU); Oliver C. Mullins, Ridgefield, CT (US); Li Jiang, Cambridge (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 286 days.

(21) Appl. No.: 10/444,586

(22) Filed: May 23, 2003

(65) Prior Publication Data

US 2005/0269499 A1    Dec. 8, 2005

(51) Int. Cl.
    *G01V 5/08* (2006.01)
(52) U.S. Cl. .................................................. 250/269.1
(58) Field of Classification Search ............. 250/269.1, 250/256
    See application file for complete search history.

(56) References Cited

U.S. PATENT DOCUMENTS

| 5,859,430 | A | 1/1999 | Mullins et al. |
| 6,037,592 | A | 3/2000 | Sunshine et al. |
| 6,465,775 | B2 | 10/2002 | Mullins et al. |
| 6,627,873 | B2 * | 9/2003 | Tchakarov et al. .......... 250/256 |
| 6,850,013 | B1 * | 2/2005 | Ashley et al. ........... 315/169.1 |
| 6,880,402 | B1 * | 4/2005 | Couet et al. .................. 73/579 |
| 2005/0063444 | A1 * | 3/2005 | Frick ........................... 372/92 |

FOREIGN PATENT DOCUMENTS

| WO | 00/02263 A1 | 1/2000 |
| WO | 01/31328 A1 | 5/2001 |
| WO | 01/63094 A1 | 8/2001 |
| WO | 02/07229 A1 | 1/2002 |
| WO | 02/07230 A1 | 1/2002 |
| WO | 02/084334 A1 | 10/2002 |

OTHER PUBLICATIONS

Biefeld, R.M., Allerman, A.A. and Kurtz, S.R., "Recent advances in mid-infrared (3-6 $\mu$m) emitters", *Materials Science Engineering,* B51, 1-8 (1998).
Allerman, A.A., Kurtz, S.R., Biefeld, K.C., Baucom, K.C. and Burkhart, J.H., "Development of InAsSb-based light emitting diodes for chemical sensing systems", *SPIE,* 3279, 126-133 (1998).
Kost, A.R., "Materials for mid-infrared semiconductor lasers", *Mat. Res. Soc. Symp.,* 484, 3-10 (1998).
Aidaraliev, M., Zotova, N.V., Karandashev, S.A., Matveev, B.A., Remennyi, M.A., Stus', N.M. and Talalakin, G.N. "Light emitting diodes for the spectral range $\lambda$=3.3-4.3 $\mu$m fabricated from the InGaAs and InAsSbP-based solid solutions: electroluminescence in the temperature range 20-180oC", *Semiconductors,* 34, 104-107 (2000).

(Continued)

*Primary Examiner*—David Porta
*Assistant Examiner*—Mindy Vu
(74) *Attorney, Agent, or Firm*—Jody Lynn DeStefanis; William L. Wang; Dale Gaudier

(57) ABSTRACT

A method of monitoring gas in a downhole environment is discussed which provides downhole a mid-infrared light emitting diode, operates the diode to transmit respective infrared signals on a first optical path extending from the diode through a downhole gas sample and a second optical path extending from the diode through a reference gas sample, detects the transmitted infrared signals, and determines the concentration of a component of the downhole gas sample from the detected signals.

32 Claims, 12 Drawing Sheets

OTHER PUBLICATIONS

Aidaraliev, M., Zotova, N.V., Karandashev, S.A., Matveev, B.A., Remennyi, M.A., Stus', N.M. and Talalakin, G.N., "Light emitting diodes for the spectral range λ=3.3-4.3 μm fabricated from InGaAs and InAsSbP solid solutions: electroluminescence in the temperature range 20-180oC (part 2)", *Semiconductors*, 35, 598-604 (2001).

Ashley, T., "Type-I InSb-based mid-infrared diode lasers", *Phil. Trans. R, Soc. Lond. A.* 359, 475-488 (2001).

Krier, A., "Physics and technology of mid-infrared light emitting diodes", *Phil. Trans. R, Soc. Lond. A.* 359, 599-618 (2001)

Stradling, R.A., "Semiconductor light sources for infrared applications: concluding remarks", *Phil. Trans. R, Soc. Lond. A.* 359, 645-658 (2001).

Faist, J., Capasso, F., Sirtori, C., Sivco, D.L., Baillargeon, J.N., Hutchinson, A.L., Chu, S-N.G. and Cho, A.Y., "High power mid-infrared (λ•~5 μm) quantum cascade lasers operating above room temperature", *Appl. Phys. Lett.*, 68, 3680-3682 (1996).

Chow, W.W., Koch, S.W. and Sargent, M., *Semiconductor-Laser Physics*, pp. 1-33, Springer, Berlin (1997).

Balkanski, M. and Wallis, R.F., *Semiconductor Physics and Applications*, pp. 353-369, Oxford University Press, Oxford (2000).

Kim, S., Erdtmann, D., Wu, E., Kass, E. Yi, H., Diaz, J. and Razeghi, M., "Photoluminescence study of InAsSb/InAsSbP heterostructures grown by low-pressure metalorganic chemical vapour deposition", *Appl. Phys. Lett.*, 69, 1614-1616 (1996).

Popov, A.A., Stepanaov, M.V., Sherstnev, V.V. and Yakolev, Y.P., "InAsSb light-emitting diodes for the detection of $CO_2$ (λ=4.3 μm)", *Tech. Phys. Lett.*, 24, 596-8 (1998).

Pullin, M.J., Hardaway, H.R., Heber, J.D., Phillips, C.C., Yuen, W.T. and Moeck, P., "Room-temperature InAsSb strained-layer superlattice light-emitting diodes at λ=4.2 μm with AlSb barriers for improved carrier confinement", *Appl. Phys. Lett.*, 74, 2384-2386 (1999).

Li, X., Heber, J., Pullin, M., Gevaux, D. and Phillips, C.C., "MBE growth of mid-infrared antimonide LEDs with strained electron barriers", *J. Crystal Growth*, 227-228, 600-604 (2001).

Biefeld, R.M., Allerman, A.A., Kurtz, S.R. and Baucom, K.C., "Progress in the growth of mid-infrared InAsSb emitters by metal-organic chemical vapour deposition", *J. Crystal Growth*, 195, 356-362 (1998).

Smith, S.D., Crowder, J.G. and Hardaway, H.R., "Recent developments in the application of mid-infrared lasers, LEDs and other solid state sources to gas detection", *SPIE*, 4651, 157-172 (2002).

Krier, A. and Sherstnev, V.V., "Powerful interface light emitting diodes for methane gas detection", *J. Phys. D: Appl. Phys.*, 33, 101-106 (2000).

Matveev, B.A., Zotova, N.V., Karandashev, S.A., Remennyi, M.A., Stus', N.M. and Talalakin, G.N., "Backside illuminated In(Ga)As/InAsSbP DH photodiodes for methane sensing at 3.3 •m", *Proc. SPIE*, 4650, 173-178 (2002).

Gao, H.H., Krier, A., Sherstnev, V. and Yakovlev, Y., "InAsSb/InAsSbP light emitting diodes for the detection of CO and $CO_2$ at room temperature", *J. Phys. D: Appl. Phys.*, 32, 1768-1772 (1999).

Pullin, M.J., Hardaway, H.R., Heber, J.D. and Phillips, C.C., "Type-II InAs/InAsSb strained-layer-superlattice negative luminescence devices", *Appl. Phys. Lett.*, 75, 3437-3439 (1999).

Elliott, C.T., "Negative luminescence and its applications", *Phil. Trans. R. Soc. Lon. A* 359, 567-579 (2001).

Olafsen, L.J., Vurgaftman, I., Bewley, W.W., Felix, C.L., Aifer, E.H., Meyer, J.R., Waterman, J.R. and Mason. W., "Negative luminescence from type-II InAs/GaSb superlattice photodiodes", *Appl. Phys. Lett.*, 74, 2681-2683 (1999).

Ashley, T., Gordon, N.T. and Phillips, T.J., "Optical modeling of cone concentrators for positive and negative IR emitters", *J. Mod. Optics*, 46, 1677-1696 (1999).

Welford, W.T. and Winston, R., *The Optics of Non-Imaging Concentrators*, pp. 1-6, Academic Press, New York (1978).

Ashley, T., Dutton, D.T., Ellicott, N.T., Gordon, N.T. and Phillips, T.J., "Optical concentrators for light emitting diodes", *SPIE*, 3289, 43-50 (1998).

Matveev, B., Zotova, N., Karandashov, S., Remennyi, M., Il'inskaya, N., Stus', N., Shustov, V., Talalakin, G. and Malinen, J., "InAsSbP/InAs LEDs for the 3.3-5.5 μm spectral range", *IEE Proc.-Optoelectron.*, 145, 254-256 (1998).

Matveev, B.A., Zotova, N.V., Karandashev, S.A., Remennyi, M.A., Stus', N.M and Talalakin, G.N., "Towards longwave (5-6 μm) LED operation at 80° C.: injection or extraction of carriers?", *IEE Proc.-Optoelectron.*, 149, 33-35 (2002).

Jones, R.C., "Immersed radiation detectors", *Appl. Opt.*, 1, 607-613 (1962).

Smith, S.D., Vass, A., Karpushko, F., Hardaway, H. and Crowder, J.G., "The prospects of LEDs, diode detectors and negative luminescence in infrared sensing of gases and spectroscopy", *Phil. Trans. R. Soc. Lond. A*, 621-634 (2001).

Matveev, B.A., Aydaraliev, M., Zotova, N.V., Karandashov, S.A., Remennyi, M.A., Stus', N.M., Talalakin, G.N., Malyutenko, V.K. and Malyutenko, O.Y., "Negative luminescence from InAsSbP diodes in the 4.0-4.3 μm range", *SPIE*, 4285, 109-116 (2001).

Crowder, J.G., Elliott, C.T. and Hardaway, H.R., "High performance, large area, uncooled detectors for mid-infrared wavelengths", *Electron. Lett.*, 37, 116-118 (2001).

Krier, A. and Mao, Y., "High performance uncooled InAsSbP/InGaAs photodiodes for the 1.8-3.4•m wavelength range", *Infrared Physics & Technology*, 38, 397-403 (1997).

Matveev, B., Aidaraliev, M., Gavrilov, G., Zotova, N., Karandashov, S., Sotnokova, G., Stus', N., Talalakin, G., Il'inskaya, N. and Alexandrov, S., "Room temperature InAs photodiode-InGaAs LED pairs for methane detection in the mid-IR", *Sensors Actuators B* 51, 233-237 (1998).

Kane, M.J., Braithwaite, G., Emeny, M.T., Lee, D., Martin, T. and Wright, D.R., "Bulk and surface recombination in $InAs/AlAs_{0.16}Sb_{0.84}$ 3.45 μm light emitting diodes", *Appl. Phys. Lett.*, 76, 943-945 (2000).

Matveev, B.A., Gavrilov, G.A., Evstropov, V.V., Zotova, N.V., Karandashov, S.A., Sotnikova, G.Y., Stus', N.M., Talalakin, G.N. and Malinen, J., "Mid-infrared (3-5 μm) LEDs as sources for gas and liquid sensors", *Sensors Actuators B* 38-39, 339-343 (1997).

Krier, A., Sherstnev, V.V. and Gao, H.H., "A novel LED module for the detection of $H_2S$ at 3.8 μm", *J. Phys. D: Appl. Phys.*, 33, 1656-1661 (2000).

Schlumberger, *Wireline Formation Testing and Sampling*, Schlumberger Wireline and Testing, Houston (1996), 2-4—2-6.

Harris, D.C., *Materials for Infrared Windows and Domes*, pp. 12-62, SPIE, Bellingham, WA, USA (1999).

Phillips, W.J., "Band-model parameters for 4.3 μm $CO_2$ band in the 300-1000 K temperature region", *J. Quant. Spectrosc. Radiat. Transfer*, 48, 91-104 (1992).

Riedl, M.J., *Optical Design Fundamentals for Infrared Systems*, pp. 146-147, 2nd ed., SPIE Press, Bellingham WA, USA (2001).

Strong, K., Taylor, F.W., Calcutt, S.B., Remedios, J.J. and Ballard, J., "Spectral parameters of self- and hydrogen-broadened methane from 2000 to 9500 cm-1 for remote sounding of the atmosphere of Jupiter", *J. Quant. Spectrosc. Radiat. Transfer*, 50, 363-429 (1993).

Bertie, J.E. and Lan, Z., "Infrared intensities of liquids XX: the intensity of the OH stretching band of liquid water revisited, and the best current values of the optical constants of $H_2O(l)$ at 25° C. between 15,000 and 1 $cm^{-1}$", *Appl. Spectrosc.*, 50, 1047-1057 (1996).

Harrick, N.J., *Internal Reflection Spectroscopy*, pp. 27-33, John Wiley, New York (1967).

Moewyn-Hughes, E.A., *Physical Chemistry*, pp. 372-375, Pergamon Press, London (1957).

Berthezene, N., de Hemptinne, J.-C., Audibert, A. and Argiller, J.-F., "Methane solubility in synthetic oil-based drilling muds", *J. Pet. Sci. Tech.*, 23, 71-81 (1999).

Glasstone, S., *Textbook of Physical Chemistry*, 2nd edition, pp. 528-530, Macmillan, London (1956).

Lechuga-Fossat, L., Flaud, J.-M., Camy-Peyret, C. and Johns, J.W.C., "The spectrum of natural hydrogen sulfide between 2150 and 2950 $cm^{-1}$", *Can. J. Phys.*, 62, 1889-1923 (1984).

Bykov, A.D., Naumenko, O.V., Smirnov, M.A., Sinista, L.N., Brown, L.R. Crisp, J. and Crisp, D., "The infrared spectrum of $H_2S$ from 1 to 5 $\mu m$", *Can. J. Phys.*, 72, 989-1000 (1994).

Håland, K., Barrufet, H.P., Rønningsen, H.P. and Meisingset, K.K., "An empirical correlation between reservoir temperature and the concentration of hydrogen sulfide", *1999 SPE Int. Symp. Oilfield Chem.*, Houston, Texas, Feb. 1999, SPE 50763.

Larsen, E.S., Hong, W.W. and Spartz, M.L., "Hydrogen sulfide detection by UV-assisted infrared spectrometry", *Appl. Spectrosc.*, 51, 1656-1667 (1997).

Peterson, D. R. and Winnick, J., "Utilization of Hydrogen Sulfide in an Intermediate-Temperature Ceria-Based Solid Oxide Fuel Cell", *J. Electrochem. Soc.*, 145, 1449-1453 (1998).

Phillips, W.J., "Band-model parameters of the 2.7-$\mu m$ band of $H_2O$", *J. Quant. Spectrosc. Radiat. Transfer*, 43, 13-31 (1990).

* cited by examiner

——— 27°C

–•–•–• 127°C

--------- 227°C

——— $CO_2$

------- $CH_4$

—— $CO_2$

------ $CH_4$ (a)  (b)

US 6,995,360 B2

METHOD AND SENSOR FOR MONITORING GAS IN A DOWNHOLE ENVIRONMENT

FIELD OF THE INVENTION

The present invention relates to a method and a sensor for monitoring gas in a downhole environment.

BACKGROUND OF THE INVENTION

The analysis of fluid samples from hydrocarbon wells for the determination of phase behaviour and chemical composition is a critical step in the evaluation of the producibility and economic value of the hydrocarbon reserves. An important factor in determining the economic value of gas and liquid hydrocarbon reserves is their chemical composition, particularly the concentration of gaseous components, such as carbon dioxide, hydrogen sulfide and methane. Similarly, the monitoring of fluid composition during production operations can have an important bearing on reservoir management decisions, such as ceasing production from certain zones or applying chemical treatments to producing wells, e.g., biocides to kill the sulfate-reducing bacteria that generate hydrogen sulfide in the near-wellbore region.

Several disclosures have described the analysis of specific gases in borehole fluids in the downhole environment using near-infrared ($\lambda$=1–2.5 $\mu$m) spectral measurements. U.S. Pat. No. 5,859,430 describes the use of near-infrared spectroscopy to determine quantitatively the presence of methane, ethane and other simple hydrocarbons in the gas phase. The gases were detected using the absorption of near-infrared radiation by the overtone/combination vibrational modes of the molecules in the spectral region 1.64–1.75 $\mu$m. More recently, U.S. Pat. No. 6,465,775 describes a method of determining the concentration of carbon dioxide in the gas phase of a wellbore fluid sample using near-infrared spectroscopy in the spectral region 1.50–2.10 $\mu$m (particularly the spectral region 1.92–2.10 $\mu$m). The radiation was generated using either a narrow band LED or laser or a broad band thermal source (e.g. a tungsten halogen lamp) with appropriate filters. The large variation in the concentration of carbon dioxide that can be experienced in wellbore fluids was accommodated using optical cells of varying path lengths. The effects of temperature on the performance of the sources, detectors and filters was compensated for by the use of a reference sample having a well-defined absorbance at each sampling temperature.

WO 01/63094 describes several methods to determine the concentration of hydrogen sulfide in wellbore fluids. One method involved the generation of a headspace above a liquid sample with the purpose of determining the concentration of hydrogen sulfide in the gas phase and hence, by means of Henry's Law, the concentration of hydrogen sulfide dissolved in the original liquid sample.

WO 02/084334 describes the use of both near- and mid-infrared spectroscopy to determine the concentration of $CO_2$ and hydrocarbons in gas samples in a borehole. The gas sample was obtained from a liquid by reducing the pressure to generate a headspace above the sample. The optical absorbance of the gas was measured either by transmission or internal reflection and a method of maintaining the transmissivity of the optical windows using wipers was described.

Smith and coworkers (16, 29) have shown the mid-infrared absorption spectra of the gases methane, carbon dioxide, nitrous oxide, nitrogen dioxide, carbon monoxide, nitric oxide, sulfur dioxide, ozone, ammonia and water vapour over the spectral region 2.5–12 $\mu$m. A number of LEDs have been fabricated with the aim of using them for the quantitative detection of various gases.

SUMMARY OF THE INVENTION

The present invention is at least partly based on the discovery that sensors based on mid-infrared LEDs can be used to monitor gases for prolonged periods at high temperatures in downhole environments.

Thus a first aspect of the present invention provides a method of monitoring gas in a downhole environment, comprising:
  providing downhole a mid-infrared light emitting diode;
  operating the diode to transmit respective infrared signals on a first optical path extending from the diode through a downhole gas sample and a second optical path extending from the diode through a reference gas sample;
  detecting the transmitted infrared signals; and
  determining the concentration of a component of the downhole gas sample from the detected signals.

Downhole temperatures typically vary between room temperature and about 200° C., but by careful control of LED spectral output and sensor configuration we have been able to operate LED-based gas sensors from room temperature up to about 200° C. for periods of up to 400 hours.

In certain circumstances it may be convenient to change the composition of the downhole gas sample before the operating, detecting and determining steps. For example, if downhole $H_2S$ levels are being monitored, this can be done indirectly by oxidising $H_2S$ in the gas sample to $SO_2$ and then determining the concentration of $SO_2$. This can be advantageous because $SO_2$ has a higher mid-infrared absorption coefficient than $H_2S$.

In preferred embodiments, a plurality of mid-infrared light emitting diodes are provided, each diode being adapted for use in a respective temperature range. The diodes are then selectively operated according to the downhole temperature. This can substantially improve the accuracy of the method at a given temperature.

Preferably, a plurality of respective photodiode detectors are provided to detect the transmitted infrared signals.

The LED may be operated in forward or reverse bias. Reverse bias operation can be particularly advantageous at elevated temperatures as the quantum efficiency of the LED can be higher under these conditions.

Preferably, the LED has a room temperature peak emission wavelength in the range from 3 to 5 $\mu$m. The identified component may be $CO_2$, $CH_4$ or $H_2S$.

Typically, the reference gas sample comprises a predetermined concentration of the gas component to be identified.

In preferred embodiments, the LED is operated to transmit a further infrared signal on a third optical path extending from the diode, the third optical path having a defined absorbance at the emission wavelength of the diode. This allows variations or uncertainties in the absorption coefficient of the gas component to be compensated for. For example, the defined absorbance may be zero.

In order to be able to monitor a range of concentrations of the gas component, the length of the first optical path may be adjusted or selected according to the expected concentration of the component.

Unwanted liquids (such as water or hydrocarbon droplets) in the gas sample or elsewhere on the first optical path can substantially impair the determination of the concentration of the gas component. Therefore, preferably, the downhole gas sample is filtered to substantially remove liquids therefrom.

Typically, the method is performed in such a way that the gas samples absorb mid-infrared light from the LED (forward bias operation) or emit mid-infrared light towards the LED (reverse bias operation) on the first and second optical paths, and the detection of the amount of absorption/emission forms the basis for the determination of the concentration of the component of the downhole gas sample. However, in alternative embodiments, the first optical path comprises a waveguide which passes through the downhole gas sample, the infrared signal on the first optical path being transmitted along the waveguide by internal reflection. Accompanying such reflection is an evanescent wave from the waveguide into the downhole gas sample and in the alternative embodiments the signal loss due to this wave can be used for the concentration determination.

A further aspect of the present invention provides a sensor for monitoring gas in a downhole environment, comprising:
  a mid-infrared light emitting diode;
  a compartment for containing a reference gas sample;
  detection means for detecting respective infrared signals transmitted on first and second optical paths extending from the diode, the apparatus being arranged such that in use the first optical path traverses a downhole gas sample and the second optical path traverses said compartment; and
  a processor for determining the concentration of a component of the downhole gas sample from the detected signals.

Thus the sensor is configured to perform the method of the previous aspect. The sensor may be further configured (e.g. comprise further features) to enable it to perform any one or combination of the optional/preferred features of the method.

Additionally or alternatively, the sensor may further comprise: at least one optical window on the first optical path, the window defining a boundary of the downhole gas sample; and an ultrasonic cleaner for removing liquid from the surface of the or each window. We have found that ultrasonic cleaners deployed in this way can be particularly effective at removing unwanted liquids.

However, in some embodiments the sensor comprises a waveguide which passes through the downhole gas sample, the infrared signal on the first optical path being transmitted along the waveguide by internal reflection. In these embodiments the sensor may further comprise an ultrasonic cleaner for removing liquid from the surface of the waveguide.

The sensor may be located downhole.

A further aspect of the present invention provides a well tool comprising the sensor of the previous aspect. For example, the well tool may be a production logging tool or a wireline sampling tool.

BRIEF DESCRIPTION OF THE DRAWINGS

Specific embodiments of the present invention will now be described with reference to the following drawings in which.

DETAILED DESCRIPTION

Mid-infrared LEDs

Figure 1:
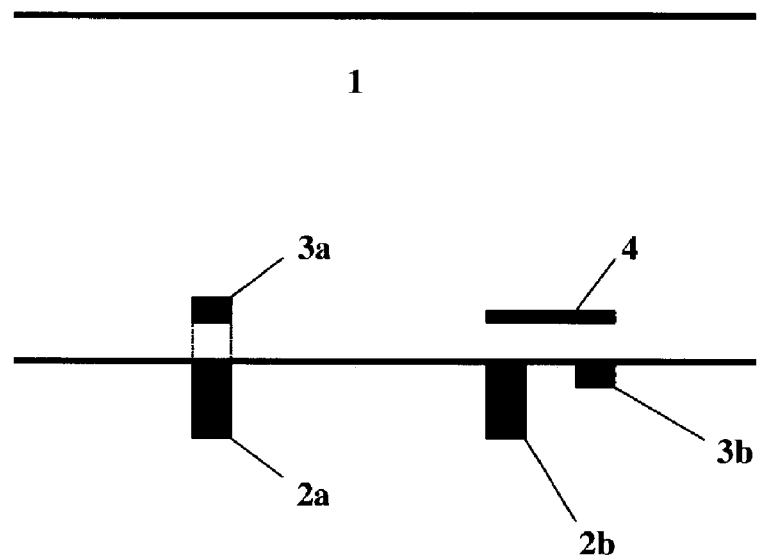
FIG. 1 shows a schematic diagram of a flow line in a tool deployed in a wellbore.

The present invention relates to the use of mid-infrared LEDs in a downhole environment. It is useful first to review mid-infrared LED technology in more detail, before considering examples of the present invention.

LEDs that radiate light in the mid-infrared spectral region (2.5–8 $\mu$m) have been studied and their fabrication described in a number of publications (1–5). Commonly, the LEDs are constructed from mixtures of group III–V elements, such as GaAs (gallium arsenide), InAs (indium arsenide), InSb (indium antimonide), InGaSb (indium gallium antimonide), InAsSb (indium arsenic antimonide) and InGaAs (indium gallium arsenide). A variety of alloys with compositions such as $InAs_xSb_yP_z$ (x+y+z=1) and $Al_xGa_yAs$ (x+y=1) have also been used for the active elements in LEDs. The composition and performance of a range of III–V mid-infrared LEDs have been summarised by Stradling (6).

The LEDs described herein are distinct from mid-infrared diode lasers. Although the materials and structures used to fabricate diode lasers are somewhat similar to those used to realise LEDs, the former are designed to yield high power densities and a narrow spectral output. Further, it has proven difficult to operate mid-infrared laser diodes at ambient temperatures without the use of optical pumping or strong magnetic fields (~1 T).

A number of methods have been used to fabricate mid-infrared LEDs, including liquid phase epitaxy (3, 5, 12), molecular beam epitaxy (13, 14) and metal organic chemical vapour deposition (15). Smith et al. (16) have summarised the fabrication of a range of mid-infrared LEDs operating in the spectral region 3–8 $\mu$m. Several distinct structures have been used to fabricate mid-infrared LEDs. Krier (5) has identified liquid phase epitaxy as a cost-effective method of producing mid-infrared LEDs. Incorporation of low concentrations of rare earth metals, such as gadolinium and dysprosium, to InAs during liquid phase epitaxial growth can reduce the background carrier concentration, thus suppressing Shockley-Read-Hall recombination, and increase the quantum efficiency of the LEDs.

Several different diode architectures have been used to construct mid-infrared LEDs using these fabrication techniques. Liquid phase epitaxy has been used to fabricate single (2) and double (17, 18) heterostructure LEDs. The single heterostructures consist of a junction of p- and n-type InGaAs or p- and n-type InAsSbP grown on an InAs substrate, while the double heterostructures consist of a thin layer (~1 $\mu$m) of InAs sandwiched between layers of p- and n-type InAsSbP cladding. Variants of the double heterostructure LEDs have been fabricated that involve the use of an InAsSb grading layer between the InAs substrate and the InAsSbP cladding layer to reduce lattice mismatch (12, 19). Molecular beam epitaxy has been used to generate LEDs with a single strained quantum well heterostructure (14) generated by an ultra thin (~20 nm) layer of InAsSb sandwiched between confining layers of intrinsic InAs, which are in turn sandwiched between p- and n-type InAs. An ultra thin (~20 nm) strained layer of InAlAs was placed between the p-type InAs substrate and the intrinsic InAs to provide an electron-confining barrier. Molecular beam epitaxy has also been used to fabricate strained-layer superlattice LEDs (13, 20) that consisted of alternating layers of InAs and InAs$_{0.914}$Sb$_{0.086}$, which were 12 nm each in thickness, grown on InAs substrates coated with a 20 nm AlSb barrier layer. Biefeld and coworkers (1) have used metal organic chemical vapour deposition to generate both multiple quantum well and strained-layer superlattice LEDs. For example, a multiple quantum well device was fabricated with 10 quantum wells consisting alternating 20 nm films of InAs$_{0.88}$Sb$_{0.12}$ and InAs deposited on a substrate of InAs coated with layers of GaAsSb and AlAsSb.

The diode structures described above emit infrared radiation when a current is passed in normal forward bias. However, when a current is applied under conditions of reversed bias, some LED devices exhibit so-called negative luminescence and become net absorbers of infrared radiation. The emission of radiation from these devices under reverse bias is less than that of a blackbody at the same temperature, i.e. the emissivity of the diode corresponds to a blackbody at a lower temperature. The principles of negative luminescence in narrow-gap semiconductor devices have recently been presented by Elliott (21), together with an outline of a gas sensor that drives the LED source in both forward and reverse bias. Olafsen et al. (22) have demonstrated negative luminescence in an InAs/GaSb superlattice diode grown by molecular beam epitaxy.

The efficient extraction of the infrared radiation emitted by LEDs has been studied by a number of groups. The high refractive index (n$\geq$3.5) of the semiconductors used to fabricate mid-infrared LEDs results in a small critical angle (<17°) and a narrow escape cone for the infrared radiation, such that typically only about 5% of the radiation generated is emitted from the diode. Ashley et al. (23) have modelled the emission and absorption of infrared radiation from an LED grown on an InSb substrate in the form of an optical cone concentrator (24). Ashley et al. found that optimal extraction for a truncated (Winston) cone was obtained when the ratio of the upper and lower surfaces was n$^2$, where n is the refractive index of the semiconductor. Ashley et al. (25) described the fabrication of an InSb parabolic reflector using a step-wise etching process. The transmissivity of the InSb in the wavelength region 3–7 $\mu$m was increased by doping with tellurium. Matveev et al. (26, 27) described the fabrication of an LED to minimise the self-absorption of the infrared radiation, particularly in the longer wavelength range ($\lambda$>4 $\mu$m), and to increase its radiation output. In order to reduce absorption losses in the LED the electrical contact to the outer (emitting or window) n-doped InAsSbP layer was mounted on the back of the LED and the InAs substrate and part of the outer n-type InAsSbP were removed by chemical etching. The optical output of the LED was further improved by the formation of a truncated conical groove in the LED that directed the internally reflected radiation on to the window layer. Matveev et al. (18) have also described the use of a CdSb immersion lens coupled to an LED using a chalcogenide-based adhesive to extract the emitted infrared radiation. Smith et al. (16), based on the earlier work of Jones (28), have described the use of two types of immersion lens where the refractive index n of the lens material is the same as that of the LED. The first type of immersion lens was a hemispherical lens with the LED located at the centre of the sphere. Both the apparent area of the source and the radiation output were increased by a factor of n$^2$, provided the diameter of the sphere was at least n times that of the source. The second type of immersion lens was a so-called hypersphere, which consisted of a sphere of radius r truncated a distance r/n from the centre of the sphere. The apparent area of the source was increased by n$^4$ and the half-angle of the emission cone of the radiation was reduced to sin$^{-1}$(1/n), thus ensuring that the radiance of the LED was unchanged by the presence of the lens. Smith et al. (29) have summarised the increases in emitted power and source area by the use of immersion lenses. WO 02/07229 describes the use of a mirror electrode on the back face of an LED with an optical focusing, interference (Fresnel lens) or diffractive (grating) element on the front of the diode from which the radiation is emitted. WO 02/07230 further describes the use of an additional layer on the emitting side of an LED that consists of a diffractive or interference optical element. The optical element, which ideally has a refractive index of within 0.3 of the semiconductor LED, can be formed by etching or ion beam milling.

The operating temperature of semiconductor diodes emitting infrared radiation in the spectral range 2–5 $\mu$m has been a key issue in their development. Considerable emphasis has been placed on the fabrication of LEDs that are capable of operating at ambient temperatures (~25° C.) in order to find use as gas sensors for environmental and medical applications. However, several issues in the operation of mid-infrared LEDs at variable and elevated temperatures have been identified. Firstly, the power output of the LEDs decreases with increasing temperature. Matveev and coworkers (3) have demonstrated an approximately logarithmic decrease in the output power of an LED with increasing temperature up to 150° C. and an exponential decrease for temperatures in the range 150–180° C. Smith et al. (16) observed that the output power of an LED decreased linearly with temperature over the range 0–50° C. Smith et al. also observed that over the temperature range 0–30° C. the temperature dependence of normal electroluminescence and negative luminescence, respectively obtained by operating the LED in forward and reverse bias, are approximately equal in magnitude but opposite in sign, i.e. the intensity of negative luminescence increases with increasing temperature. Matveev et al. (27) demonstrated that for an LED emitting in the mid-infrared spectral region ($\lambda=5.3\,\mu m$) the logarithm of the output power decreased linearly with increasing temperature over the range 20–85° C. Conversely, the negative luminescence increased by a comparable rate over the same temperature range. Matveev et al. also showed that the conversion efficiency of the LED decreased from 18 to 6.5 $mW/cm^2 A$ as the temperature increased from 20 to 85° C. WO 00/02263 discloses the use of the difference between positive and negative electroluminescence from a mid-infrared LED to give an optical output that is substantially independent of temperature over the range 0–35° C. The alternating forward and reverse bias was applied to the LED at a frequency of 1–5 Hz. Matveev et al. (33) have compared the expected power output of several LEDs generating both positive and negative luminescence in the spectral range 3.3–6.0 $\mu m$ and over the temperature range 20–200° C.

A second issue is the shift in the spectral output of the LEDs with increasing temperature. Matveev and coworkers (3, 18, 27) have shown that the wavelength of the maximum intensity of the emitted radiation, denoted $\lambda_{max}$, increases with increasing temperature. For example, for one LED, $\lambda_{max}$ increased from 3.3 $\mu m$ at 26° C. to 3.8 $\mu m$ at 176° C. (3), while for a second LED, $\lambda_{max}$ increased from 5.3 to 5.6 $\mu m$ as the temperature increased from 20 to 65° C. (27). In contrast, Smith et al. (16) have reported a change in $\lambda_{max}$ from 4.4 to 4.1 $\mu m$ as the temperature increased from 0 to 50° C. An increase in $\lambda_{max}$ with increasing temperature is expected as the band gap energy decreases with increasing temperature for most semiconductors. For example, Matveev et al. (3) have shown that the temperature coefficient of the band gap energy for two LEDs with nominal $\lambda_{max}$ values of 3.3 and 4.3 $\mu m$ at ambient temperature was $-0.35$ meV/° C., which corresponds to a shift in $\lambda_{max}$ of 3 nm/° C.

A further aspect in the development of solid-state gas sensors is the choice of detector. Semiconductor photodiodes having similar structures to LEDs have been developed and are suitable for use at ambient and elevated temperatures. Smith et al. (29) have compared the performance of an InSb photodiode with the typical performance of pyroelectric and photovoltaic detectors. Detectivity (D*) values of $3-5\times10^9$ cm $Hz^{1/2}/W$ were reported for an InSb diode (34) immersed in a germanium hypersphere. Krier and Mao (35) reported the performance of an InGaAs photodiode detector grown on an InAs (p+) substrate by liquid phase epitaxy and capped with a InAsSbP window. The measured detectivity of the photodiode was $1.2\times10^{10}$ cm $Hz^{1/2}/W$ over the wavelength range 2.0–3.2 $\mu m$ at 27° C., a value that compared favourably with commercially available PbSe and InAs detectors at the same temperature. Matveev et al. (18) have described the fabrication and evaluation of an InGaAs photodiode, which consisted of a layer of n-InGaAs sandwiched between p- and n-type InAsSbP deposited on an InAs substrate using liquid phase epitaxy. The thickness of the InAs substrate was reduced by lapping to produce an optical window to which was attached a CdSe immersion lens. The detectivity of the photodiode at $\lambda=3.3$ mm and ambient temperature was reported to be $1.6\times10^{10}$ cm $Hz^{1/2}/W$. The logarithm of the photovoltaic sensitivity decreased linearly with increasing temperature from a value of 1000 V/W at 20° C. to 6 V/W at 110° C. for an InAs window thickness of 25 $\mu m$.

EXAMPLE SENSOR CONFIGURATIONS

FIG. 1 shows a schematic of a flow line 1 in a tool deployed in a wellbore. The flow line can be part of a wireline sampling tool and the gas sample can be flowed either into a sample bottle for recovery at the surface or back into the wellbore. Alternatively, the flow line can be part of a headspace apparatus designed to generate a gaseous sample from an initially liquid sample, e.g. as described in WO 01/63094. A small gas sensor, which consists of a mid-infrared LED 2a and photodiode detector 3a, is positioned in the flow line. The optical path extends directly between the LED and the photodiode. FIG. 1 also shows an alternative form of sensor in which the optical path is reflected at a mirror 4 located in the flow line between the LED 2b and the photodiode 3b.

Figure 2:
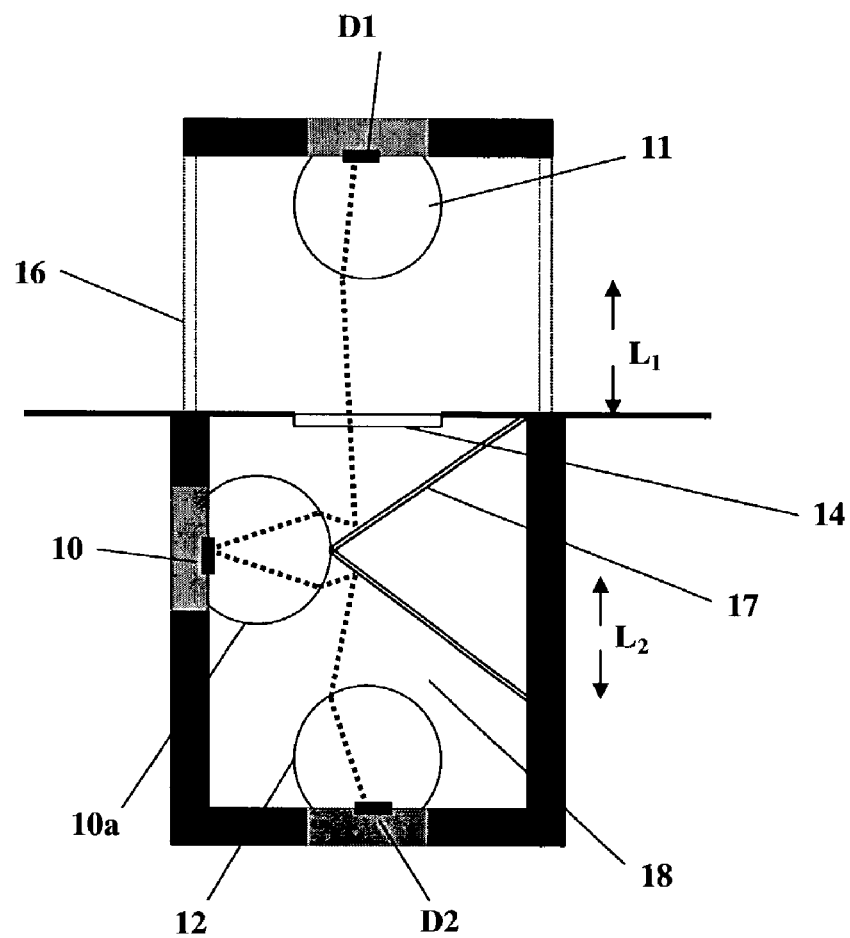
FIG. 2 shows a schematic diagram of one configuration for an LED, photodiode detectors and optics of a gas sensor.
Figure 3:
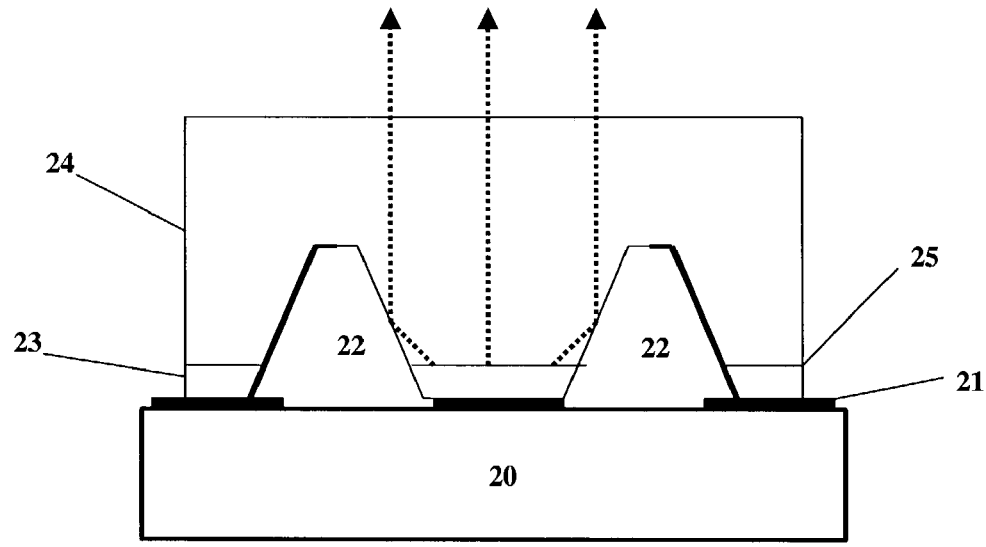
FIG. 3 shows a schematic diagram of a transverse section through an LED.

FIG. 2 shows in more detail one configuration for the LED, photodiode detector and optics of the gas sensor. The LED 10 consists of a suitable combination of III–V semiconductors to generate a narrow band gap active layer with confining layers that will emit infrared radiation in the wavelength range 2–5 $\mu m$ when a forward bias d.c. current is applied to the structure. For example, for the detection of $CO_2$ gas in the spectral range 3.5–5.5 $\mu m$ a semiconductor based on InAsSb would be suitable. The LED structure can be fabricated using liquid phased epitaxy, molecular beam epitaxy or metal organic vapour phase epitaxy, and consists of a single p-n junction, a heterostructure or a strained-layer superlattice. The structure shown in transverse section in FIG. 3, based on the LEDs fabricated by Matveev and coworkers (18, 26, 27), is particularly suitable for deployment in the gas sensors described herein as the electrical contacts are located on the back of the LED and the optical window is free from obstruction and can be coupled to an external optical system. The structure comprises an insulating substrate 20 to which is attached metal electrodes 21 and gold contacts 22. A p-n junction 25 is formed between a p-semiconductor 23 and n-semiconductor 24 which are carried as layers on the substrate. Arrows indicate typical optical paths. The infrared radiation can be efficiently extracted from the LED using an optical concentrator such as a hypersphere or a Winston cone. The refractive index $n_1$ of the cone or portion of a sphere is closely matched to the refractive index $n_2$ of the LED. The cone or hypersphere can either be bonded to the LED with a suitable non-absorbing adhesive (e.g., chalcogenide glass) or held in place by compression. Alternatively, the optical concentrator can be an integral part of the LED and grown on the external window by a step-wise etching process. FIG. 2 shows a hypersphere 10a mounted to LED 10.

Figure 4:
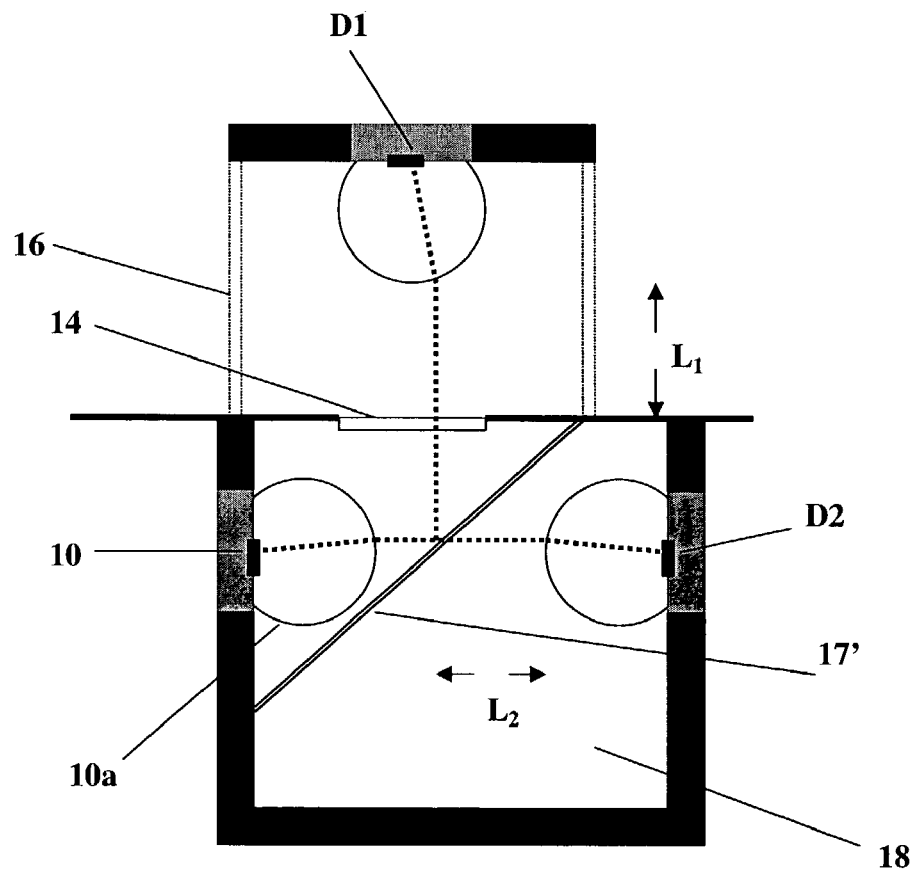
FIG. 4 shows a schematic diagram of another configuration for an LED, photodiode detectors and optics of a gas sensor.

On FIG. 2 dashed lines show typical optical paths between the LED 10 and respective detectors D1, D2, which measure the output of the LED. Each detector carries a corresponding hypersphere 11, 12 for concentrating the respective optical signal. The output is directed to the two detectors using a beam splitter 17, which consists of a portion of a toroid with the inner surface formed from two parabolas meeting at 90° at the surface of hypersphere 10a. The surface of the parabolas is coated with a reflective, non-absorbing material, such as aluminium. FIG. 4 shows schematically another configuration for the gas sensor in which an alternative form of beam splitter 17' consisting of a half-silvered mirror is used. The mirror allows one half of the signal to be reflected to detector D1 and the other half to be transmitted to detector D2.

The infrared radiation is sent to detector D1 through a thin optical window 14, which consists of an infrared-transparent material, such as synthetic diamond, chalcogenide glass (e.g. zinc selenide), yttrium oxide (yttria), sapphire or a combination of these materials, e.g. diamond-coated zinc selenide. A detailed list of materials for use as infrared windows over the wavelength range 2–20 µm has been given by Harris (46). Detector D1 is spaced a distance $L_1$ from the window, and this distance is the optical path length of the infrared radiation in the analyte gas sample. A further optical window (not shown) adjacent detector D1 may protect the detector from direct contact with the gas sample.

For gases such as $CO_2$ and $CH_4$, the downhole concentration is expected to be in the range 0.5–30 volume percent. A typical path length $L_1$ is ~1 mm but this can be varied depending on the expected concentration of the gas. For example, Pullin et al. (20) showed that the absorption of infrared radiation at λ=4.3 m due to $CO_2$ at atmospheric concentration (0.03%) over a path length of 1.1 m resulted in the response of the detector decreasing from 0.66 to 0.24 µW/meV. A similar level of absorption would be expected from a $CO_2$ concentration of 30% at ambient pressure with a path length of 1 mm. A small stepper motor (not shown) can be provided to displace detector D1 and vary $L_1$ so that a particular level of absorption can be maintained. Another option is to have an array of sensors or detectors, each with a differing value of $L_1$.

Figure 5:
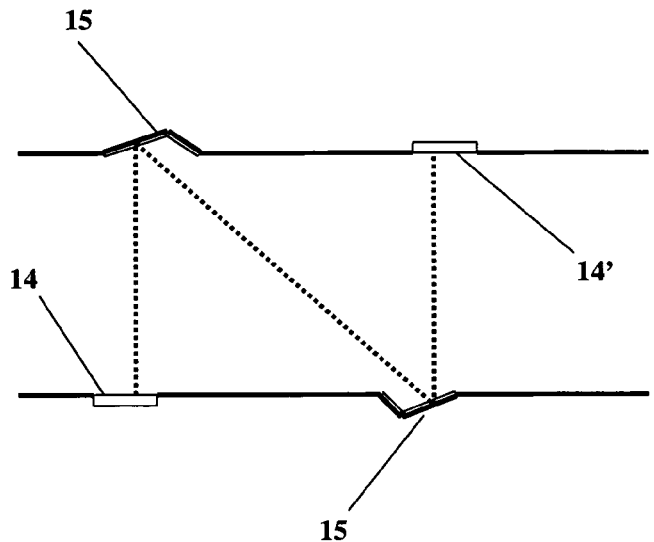
FIG. 5 shows a schematic diagram of infrared mirrors increasing the optical path between an LED and a photodiode detector.

The detection of $H_2S$ in gas samples obtained from wellbore fluids is more demanding due to both its low concentration, typically in the range 0.1–1000 ppm, and relatively weak absorptivity. For example, Krier et al. (39) showed that $H_2S$ at a concentration of 100% at ambient temperature and pressure caused the measured output power at λ=3.8 µm to decrease by a factor of two when the optical path length was 5 cm. At ambient temperature a partial pressure of 1 bar translates to a concentration of 1000 ppm at a total gas pressure of 1000 bar from which it may be seen that a decrease of 5% in the output power of the LED corresponds to an $H_2S$ concentration of 100 ppm. Lower concentrations of $H_2S$ could be detected using a longer optical path length, which can be achieved by the use of multiple reflections across the flow line. For example, FIG. 5 shows schematically infrared mirrors 15 which increase the optical path between optical windows 14, 14' respectively covering the LED and detector D1. The mirrors can be made of a polished surface coated with gold.

Returning to FIGS. 2 and 4, optical window 14 is protected from particulate material and liquid droplets by mechanical filters 16, which allow the passage of gas but not particles or drops. The infrared gas sensor has a low tolerance to liquid water or hydrocarbons in the optical path between LED 10 and detector D1 due to the high molar concentrations of the pure liquids, e.g. 55.6 moles per liter for pure water.

The optical signal directed to detector D2 is a reference signal which enables the effects of temperature and pressure on the spectral properties of the LED, photodiode detectors and gaseous species on the measured absorbance at detector D1 to be compensated for. Length $L_2$ of the optical path between beam splitter 17 and detector D2 is contained within a reference gas compartment 18 filled with the particular gas being analysed by the sensor at a known concentration in an inert diluent, such as nitrogen or helium. The reference gas sample can be connected to the flow line by a suitable hydraulic link, such as a piston, set of bellows or rubber membrane, to enable the hydrostatic pressure of the reference gas sample to equal that of the test gas in the flow line.

The concentration of the particular gaseous species in the flow line is determined from the ratio of the signals of detectors D1 and D2 and the known concentration of the species in compartment 18. Applying the Beer-Lambert law, the measured intensity $I_1$ of the infrared radiation reaching detector D1 is related to the optical path length $L_1$ and concentration $C_G$ of the absorbing component in the gas by $$\frac{I_1}{\alpha I_o} = e^{-\varepsilon C_G L_1} \quad [1]$$

where $I_o$ is the output intensity of the LED, α is the fraction of the radiation from the LED directed towards detector D1 and ε is the absorption coefficient of the gas. Similarly, for the measured reference intensity $I_2$ at detector D2

$$\frac{I_2}{\beta I_o} = e^{-\varepsilon C_o L_2} \quad [2]$$

where β is the fraction of the radiation from the LED directed towards detector $D_2$ (α+β=1) and $C_o$ is the concentration of the gas in compartment 18. Eliminating $I_o$ in eqns. [1] and [2], taking natural logarithms and rearranging yields $$C_G = \frac{1}{\varepsilon L_1} \ln\left(\frac{\alpha I_2}{\beta I_1}\right) + \frac{C_o L_2}{L_1} \quad [3]$$

Thus $C_G$ is determined from measured values of $I_1$ and $I_2$ and known values of ε, $L_1$, $L_2$, α, β and $C_o$.

The reference concentration $C_o$ can either be constant or variable, depending on whether the volume of the reference sample is fixed or variable. If the volume of compartment 18 is fixed at a value of $V_o$, then $$C_o = \frac{M_o}{V_o} \quad [4]$$

where $M_o$ is the fixed mass of the reference gas sample. Alternatively, $$C_o = \frac{n}{V_o} \quad [5]$$

where n, the number of moles of gas, is given by $M_o/M_w$, where $M_w$ is the molecular weight of the gas. The partial pressure $P_i$ of the reference gas in compartment 18 is given by $$P_i = \frac{nRT}{V_o} = C_o RT \qquad [6]$$

where R is the gas constant and T the absolute temperature, assuming the gas behaves as an ideal gas. Changes in sampling temperature T causes $P_i$ to change, with $C_o$ remaining constant.

However, as mentioned above, the volume $V_o$ of compartment 18 may be change in order that the total gas pressure P in the compartment is equal to that in the flow line. For example, it may be desirable to compensate for broadening of the absorption bands of the gas caused by pressure increases (so-called collision broadening). Assuming ideal gas behaviour, the concentration of gas in the compartment is then given by $$C_o = \frac{X_o P}{RT} \qquad [7]$$

where $X_o$ is the mole fraction of the gas in the compartment.

The performance of mid-infrared LED gas sensors can be complicated by the shift in the spectral output of the LED and the detectivity of the photodiode with temperature. This problem can be overcome by the use of several LED/photodiode pairs, each pair having a different wavelength at which their output power and detectivity have maximum values at ambient temperature. For example, $CH_4$ can be detected in the spectral range 3.26–3.31 $\mu$m using two InGaAs LEDs described by Matveev et al. (3). These LEDs have a peak width $\Delta\lambda = 0.25$ $\mu$m at 50% of the intensity at $\lambda_{max}$. Furthermore $\lambda_{max}$ increases at a rate of 3 nm/° C. as the temperature increases. Taking the detection wavelength of $CH_4$ to be 3.28 $\mu$m and required output power to be $\geq 50\%$ of that at $\lambda_{max}$, one LED with $\lambda_{max} = 3.15$ $\mu$m at 25° C. will enable $CH_4$ to be detected in the temperature range 25–105° C., while a second LED with $\lambda_{max} = 2.90$ $\mu$m at 25° C. will enable $CH_4$ to be detected in the temperature range 105–185° C. Alternatively, an LED and photodiode detector can be fabricated with a significantly larger value of $\Delta\lambda$, typically in excess of 0.5 $\mu$m, so that the LED/photodiode pair can cover the entire temperature range.

The determination of the concentration $C_G$ of a particular gas in the flow line depends on knowledge of the value of the absorption coefficient $\epsilon$. For gases at elevated temperatures there can be some doubt over the value of $\epsilon$, which may compromise the measurement of $C_G$. The effects of variations or uncertainties in $\epsilon$ can be eliminated by the use of a third detector and a modified beam splitter that allows some portion $\gamma$ of the radiation to reach this detector ($\alpha+\beta+\gamma=1$).

Figure 6:
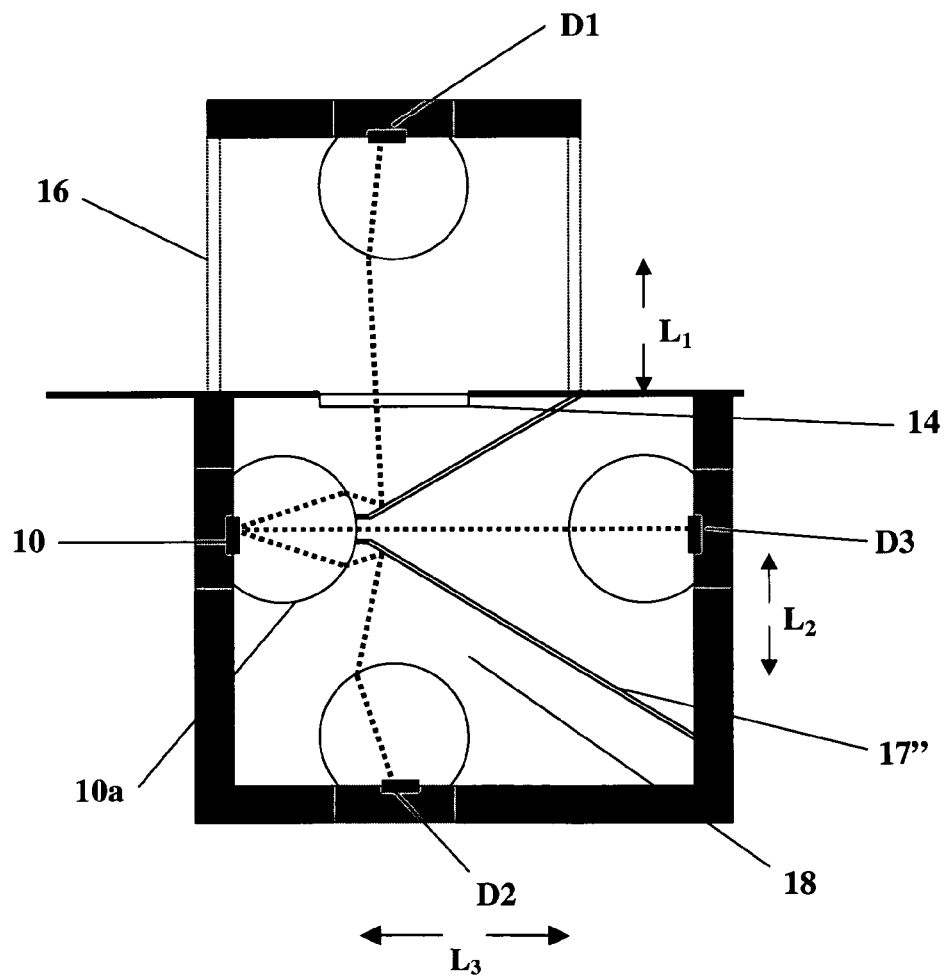
FIG. 6 shows a schematic diagram of another configuration for an LED, photodiode detectors and optics of a gas sensor.

FIG. 6 shows a schematic of a further configuration for the gas sensor with a third detector D3 and modified beam splitter 17''. The optical path length, $L_3$, between LED 10 and detector D3 contains no absorbing species. Eqns. [1] and [2] are augmented by $$I_3 = \gamma I^o \qquad [8]$$

where $I_3$ is the intensity measured by detector D3. Substitution of eqn. [8] into eqns. [1] and [2] gives $$\frac{\Upsilon I_1}{\alpha I_3} = e^{-\epsilon C_G L_1} \qquad [9]$$

$$\frac{\Upsilon I_2}{\beta I_3} = e^{-\epsilon C_o L_2} \qquad [10]$$

Taking natural logarithms, eliminating $\epsilon$ and rearranging gives $$C_G = \frac{C_o L_2}{L_1} \frac{\ln\left(\frac{\Upsilon I_1}{\alpha I_3}\right)}{\ln\left(\frac{\Upsilon I_2}{\beta I_3}\right)} \qquad [11]$$

$C_G$ is therefore determined from measured values of $I_1$, $I_2$ and $I_3$ and known values of $C_o$, $L_1$, $L_2$, $\alpha$, $\beta$ and $\gamma$.

Choice of Spectral Region

An important feature in the design of LED gas sensors is the choice of spectral region. There are two aspects to this choice. Firstly it is important to ensure that a spectral region is chosen to minimise interferences, i.e. that the measured reduction in the intensity $I_1$ is substantially due only to one chemical species. The second aspect concerns the sensitivity of the spectral measurement and can be illustrated by the example of $CO_2$. The Beer-Lambert law in logarithmic form is $$\ln\left(\frac{I_o}{I}\right) = \epsilon C L \qquad [12]$$

and a reasonable lower value of $I/I_o$ that can be reliably measured is 0.05, which yields the condition $$CL \leq \frac{3}{\epsilon} \qquad [13]$$

Figure 7:
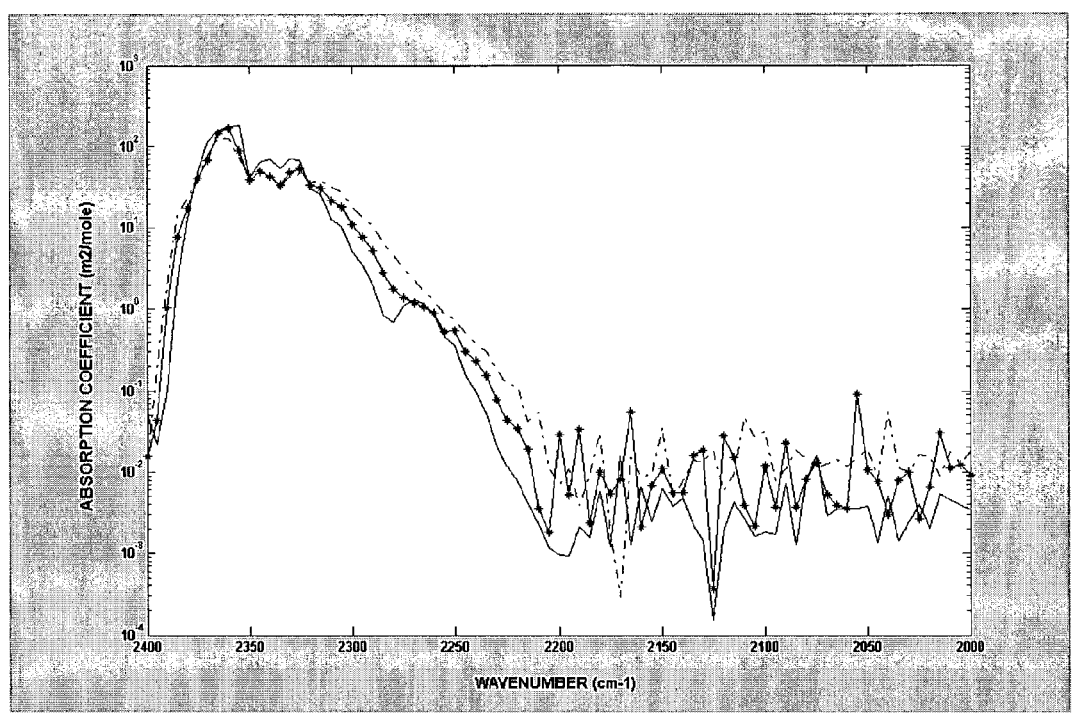
FIG. 7 shows the dependence of the absorption coefficient $\epsilon$ of $CO_2$ on the wavenumber of infrared radiation at 300, 400 and 500 K (27, 127 and 227° C. respectively)

FIG. 7 shows the dependence of the absorption coefficient $\epsilon$ of $CO_2$ on the wavenumber of the infrared radiation at 300, 400 and 500 K (27, 127 and 227° C. respectively) based on 25 cm$^{-1}$ resolution data presented by Phillips (47). If the LED is operating in the spectral region 2370–2350 cm$^{-1}$ ($\lambda = 4.22$–4.25 $\mu$m), then the value of $\epsilon$ is in the range 100–200 m$^2$/mole and CL must be less than 0.015 mole/m$^2$. This value of CL translates to a concentration C of less than 0.015 moles per liter (0.66 grams per liter) for an optical path length of 1 mm. The choice of spectral region will therefore determine the concentration range over which the sensor can operate for a given range of optical path lengths. For example, if the LED is operating in the spectral range 2300–2260 cm$^{-1}$ (4.35–4.42 $\mu$m) where the average value of $\epsilon$ is approximately 5 m$^2$/mole, then the upper value of C is 0.6 moles per liter (26.4 grams per liter) for a path length of 1 mm. Similarly, in the spectral range 2260–2200 cm$^{-1}$ ($\lambda = 4.43$–4.55 $\mu$m) the average value of $\epsilon$ is approximately 0.05 m$^2$/mole, which corresponds to an upper concentration of $CO_2$ of 60 moles per liter (2640 grams per liter) with an optical path length of 1 mm. This last concentration of $CO_2$ is equivalent to pure $CO_2$ gas at a pressure of 27,000 psi and a temperature of 100° C., assuming ideal gas behaviour.

The spectral output of the LED can be confined to a particular narrow wavelength range by the use of narrow bandpass interference filters (48) to overcome problems of spectral interference by other components. Typically, the spectral width of the filter can be 50–100 nm to ensure that the concentration of the gaseous species is determined over a specific wavelength region to ensure minimal spectral interferences and optimal sensitivity.

$CO_2$ Detection Example

A $CO_2$ gas detector may consist of two sensors that operate over two different temperature ranges. The first sensor operates over the temperature range 25–105° C. and the second operates over the temperature range 105–185° C. The need for two sensors having respective LEDs arises from the shift in $\lambda_{max}$ with temperature and the width of the spectral output.

Each $CO_2$ gas sensor has the configuration of FIG. 2 including a reference gas compartment of variable volume to allow the determination of the concentration of $CO_2$ in a flow line at 125° C. and a pressure of 5,600 psi (381.0 bar). The reference concentration of $CO_2$ gas is $C_o$=2 moles per liter of nitrogen gas diluent at 125° C. and 5,600 psi (381.0 bar). Assuming the carbon dioxide/nitrogen mixture behaves as an ideal gas, the concentration of $CO_2$ in the reference compartment corresponds to 24.5 weight percent. The optical path length $L_2$ is fixed at a value of 2 mm.

The output power of the LED is 5.2 mW/cm$^2$A at 125° C. The active area of the LED is 4 mm$^2$, which with a forward bias current of 1.5 A, gives an output power of 0.31 mW. The optical system of FIG. 2 is subject to 50% losses due to reflection and absorption and the beam splitter is designed to give $\alpha=\beta=0.5$. The spectral region chosen to determine the concentration of $CO_2$ is 2260–2200 cm$^{-1}$ ($\lambda$=4.42–4.55 $\mu$m) where the average value of $\epsilon$ is 0.1 m$^2$/mole and a filter is applied to the LED to restrict the output infrared radiation to this spectral range. The filter rejects 80% of the output radiation from the LED. The half-width of the output radiation of the LED is 0.25 $\mu$m and the value of $\lambda_{max}$ of the LED's output spectrum increases with increasing temperature at a rate of 3 nm/° C. The LED is constructed to give a value of $\lambda_{max}$ of 4.13 $\mu$m at 25° C., such that $\lambda_{max}$ shifts to 4.38 $\mu$m at 125° C.

The sensitivity of detectors D1 and D2 is 8.5 V/W and both detectors generate a voltage of 0.14 mV in the absence of $CO_2$ in the optical path lengths $L_1$ and $L_2$. The presence of the $CO_2$ in the reference compartment reduces the measured voltage from detector D2 to 0.094 mV. $L_1$=3 mm and the presence of the concentration Cc in the flow line reduces the detected voltage to 0.109 mV. From eqn. [3], $C_G$ is 0.84 moles per liter, which, assuming the remaining gas is methane and the methane/carbon dioxide mixture acts as an ideal gas, is equivalent to a concentration of 17.6 weight percent.

$CH_4$ Detection Example

The detection of $CH_4$ can be achieved using a similar gas detector based on a pair of LEDs operating in the wavelength range 2.9–3.5 $\mu$m. The spectral output from the two LEDs has a peak width of 0.25 $\mu$m and the $\lambda_{max}$ value of the output increases with increasing temperature at a rate of 3 nm/° C. The first LED, characterised by $\lambda_{max}$=3.16 $\mu$m at 25° C., operates in the temperature range 25–105° C., while the second LED, with $\lambda_{max}$=2.91 $\mu$m at 25° C., operates in the temperature range 105–185° C.

The $CH_4$ sensor is deployed with a reference compartment of fixed volume containing a fixed amount of $CH_4$ and nitrogen. $L_2$=2 mm, the reference compartment volume is 10 mm$^3$ $\mu$and the methane concentration is 8 moles per liter (128 grams per liter); the nitrogen concentration is also 8 moles per liter (224 grams per liter). The temperature at which the $CH_4$ measurement is made is 142° C., which, assuming the $CH_4/N_2$ mixture acts as an ideal gas, yields a pressure of 8009 psi (555 bar) in the reference compartment. The optical path length in the flow line is $L_1$=1 mm.

The output power rating of the LEDs at 142° C. is 6.1 mW/cm$^2$A, which with an active area of 4 mm$^2$ and an applied (forward bias) current of 1.8 A, gives a total output power of 0.44 mW. The optical system has losses of 45%, caused by reflection and absorption, and the beam splitter is designed with $\alpha=\beta=0.5$. The spectral region used to detect $CH_4$ is 3.27–3.32 $\mu$m and this spectral region is achieved using an interference filter that rejects 80% of the output of the LED.

Figure 8:
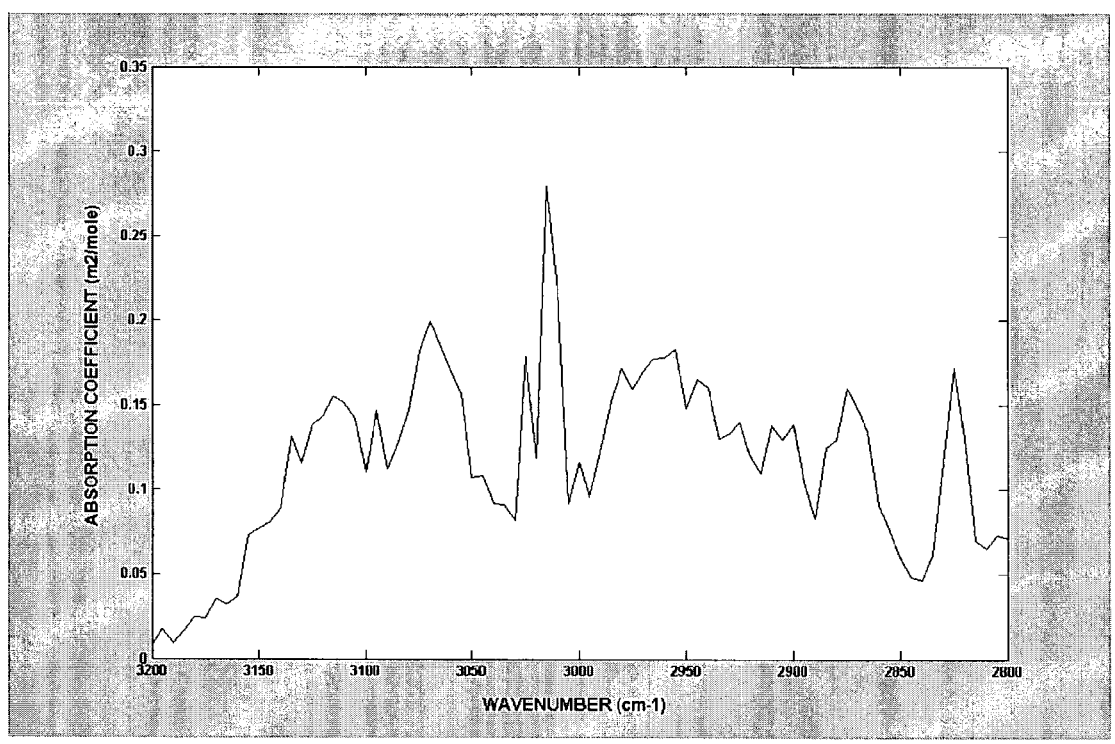
FIG. 8 shows the dependence of the absorption coefficient $\epsilon$ of $CH_4$ on wavenumber over the spectral region 3200–2800 $cm^{-1}$ ($\lambda$=3.12–3.57 $\mu$m)

FIG. 8 shows the dependence of the absorption coefficient $\epsilon$ of $CH_4$ on wavenumber over the spectral region 3200–2800 cm$^{-1}$ ($\lambda$=3.12–3.57 $\mu$m, resolution of data is 5 cm$^{-1}$) (49). The average value of $\epsilon$ over the spectral range of the measurement is 0.13 m$^2$/mole.

The sensitivity of detectors D1 and D2 is 9.1 V/W at 142° C. and the output measured by the detectors in the absence of $CH_4$ is 0.218 mV. The presence of $CH_4$ in the reference compartment reduces the output of detector D2 to 0.027 mV. The corresponding output of detector D1 is 0.039 mV and the application of eqn. [3] gives the flow line concentration of $CH_4$ as $C_G$=13.13 moles per liter (210 grams per liter).

$H_2S$ Detection Example

The detection and quantification of $H_2S$ in subsurface gas samples can be achieved by mid-infrared spectroscopy by one of several methods. Direct detection of $H_2S$ is possible using a mid-infrared LED gas sensor operating in the spectral region of 2630 cm$^{-1}$ ($\lambda$=3.80 $\mu$m), 3785 cm$^{-1}$ ($\lambda$=2.64 $\mu$m) and 4880 cm$^{-1}$ ($\lambda$=2.07 $\mu$m) where the gas has a large number of absorption bands (61, 62).

An example of the detection of $H_2S$ using a mid-infrared LED gas sensor is now presented. The $H_2S$ detector consists of a single gas sensor that operates over the temperature range 110–190° C., which encompasses the range over which the gas is most commonly encountered (63). The $H_2S$ gas sensor is deployed in a flow line to determine its concentration in a gas sample at a temperature of 140° C. and a pressure of 6150 psi (418 bar). The reference cell consists of a fixed volume of 7.85 cm$^3$ with a fixed mass of $H_2S$ (0.21 grams) diluted in a fixed mass of $CH_4$ (1.92 grams). The $H_2S$ has a mole fraction of 0.05 in $CH_4$, which is equivalent to a concentration of 9.86 weight percent or 0.80 moles per liter (27,300 ppm). The optical path length of the reference cell is $L_1$=10 cm.

The spectral region over which the concentration of $H_2S$ is to be determined is 5000–4762 cm$^{-1}$ ($\lambda$=2.0–2.1 $\mu$m) in which the average value of the absorption coefficient of $H_2S$ is 0.014 m$^2$/mole(2). The LED is designed to generate infrared radiation with a $\lambda_{max}$ value of 1.615 $\mu$m at 25° C., which increases to a value of 1.96 $\mu$m at 140° C. The value of $\lambda$max shifts by 3 nm/° C. and the peak width of the output radiation is 0.25 $\mu$m. A filter is used to limit the output radiation to the spectral region 2.0–2.1 $\mu$m, which results in 70% of the LED's output being rejected.

The output power rating of the LED at 140° C. is 6.8 mW/cm$^2$A, which, with an area of 4 mm$^2$, an applied forward current of 2.0 A and losses of 38% due to reflection and absorption losses in the optics, gives an actual power output of 0.10 mW. The beam splitter is designed to give $\alpha=\beta=0.5$. The sensitivity of detectors D1 and D2 is 11.1

V/W at 140° C. and both detectors generate a voltage of 0.56 mV in the absence of $H_2S$ in the optical path lengths $L_1$ and $L_2$. The presence of $H_2S$ in the reference cell reduced the output voltage of detector D2 to 0.20 mV. The presence of the gas sample in the optical path of the measurement cell reduces the detector voltage to 0.40 mV, which, from eqn. [3], yields a concentration of $H_2S$ of 0.237 moles per liter (8.1 grams per liter). If the remainder of the sample gas is $CH_4$, then its concentration is 12.1 moles per liter (193.6 grams per liter) and the concentration of $H_2S$ can be expressed as 4.0 weight percent.

Detection of $CO_2$ in $CH_4$

The detection of $CO_2$ in wellbore gas samples will typically requires the measurement to be made in a matrix of methane and other light hydrocarbons, such as ethane and propane. An important aspect of LED gas detectors is that $CO_2$ can be detected with minimal interference from $CH_4$.

Figure 9:
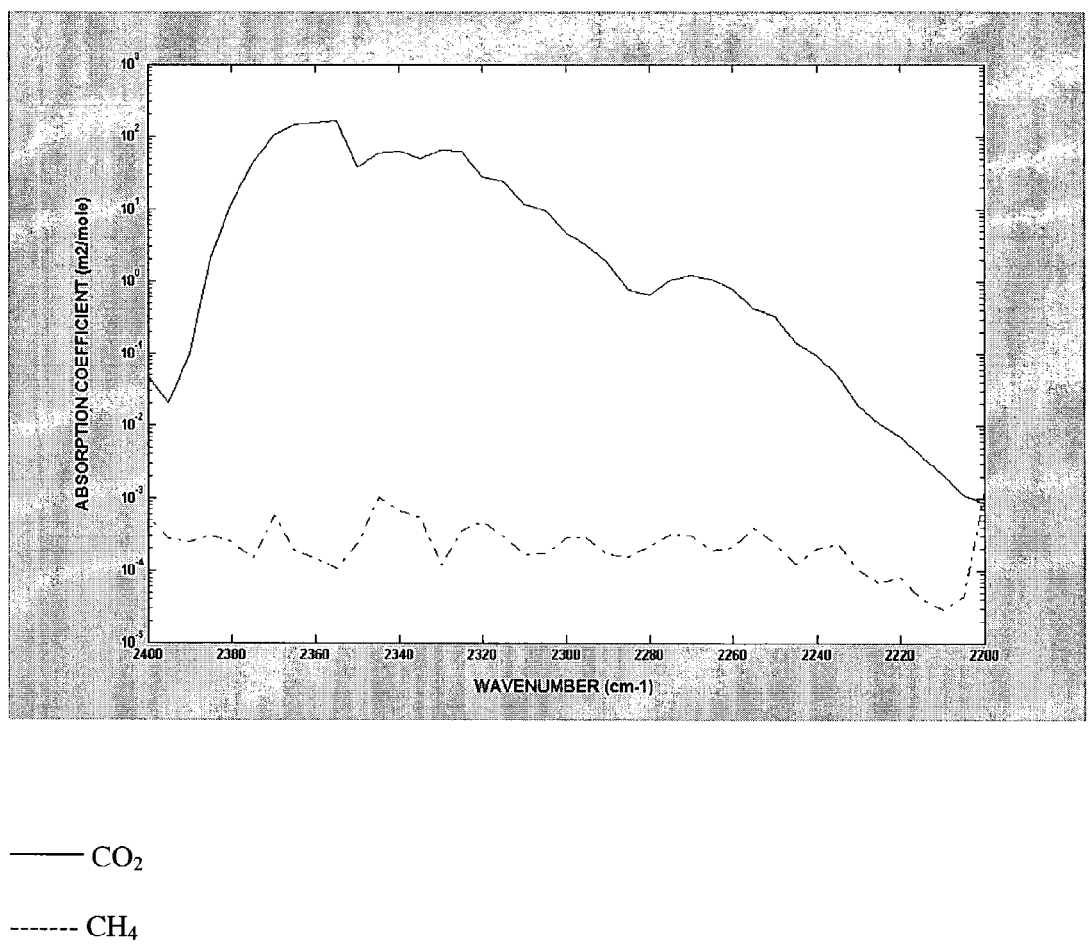
FIG. 9 shows a comparison of the absorption coefficient $\epsilon$ of $CO_2$ and $CH_4$ over the spectral region 2400–2240 $cm^{-1}$ ($\lambda$=4.17–4.46 $\mu$m)

FIG. 9 shows a comparison of the absorption coefficient $\epsilon$ of $CO_2$ and $CH_4$ over the spectral region 2400–2200 cm$^{-1}$ ($\lambda$=4.17–4.55 $\mu$m). The average value of $\epsilon$ for $CH_4$ over this spectral range is 5×10$^{-4}$ m$^2$/mole, which is almost 6 orders of magnitude below the peak value of $\epsilon$ for $CO_2$, 4 orders of magnitude lower than the value of $\epsilon$ for $CO_2$ in the spectral region 2300–2260 cm$^{-1}$ (4.35–4.42 m), and 1–2 orders of magnitude lower in the range 2260–2200 cm$^{-1}$ (4.43–4.55 $\mu$m) The choice of spectral region will depend on the relative concentrations of $CO_2$ and $CH_4$. When the $CO_2/CH_4$ ratio is small, the concentration of $CO_2$ can be determined using an LED operating in the spectral region 2380–2320 cm$^{-1}$ ($\lambda$=4.20–4.31 $\mu$m), while the region 2300–2200 cm$^{-1}$ ($\lambda$=4.35–4.55 $\mu$m can be used when the $CO_2/CH_4$ ratio is larger.

Figure 10:
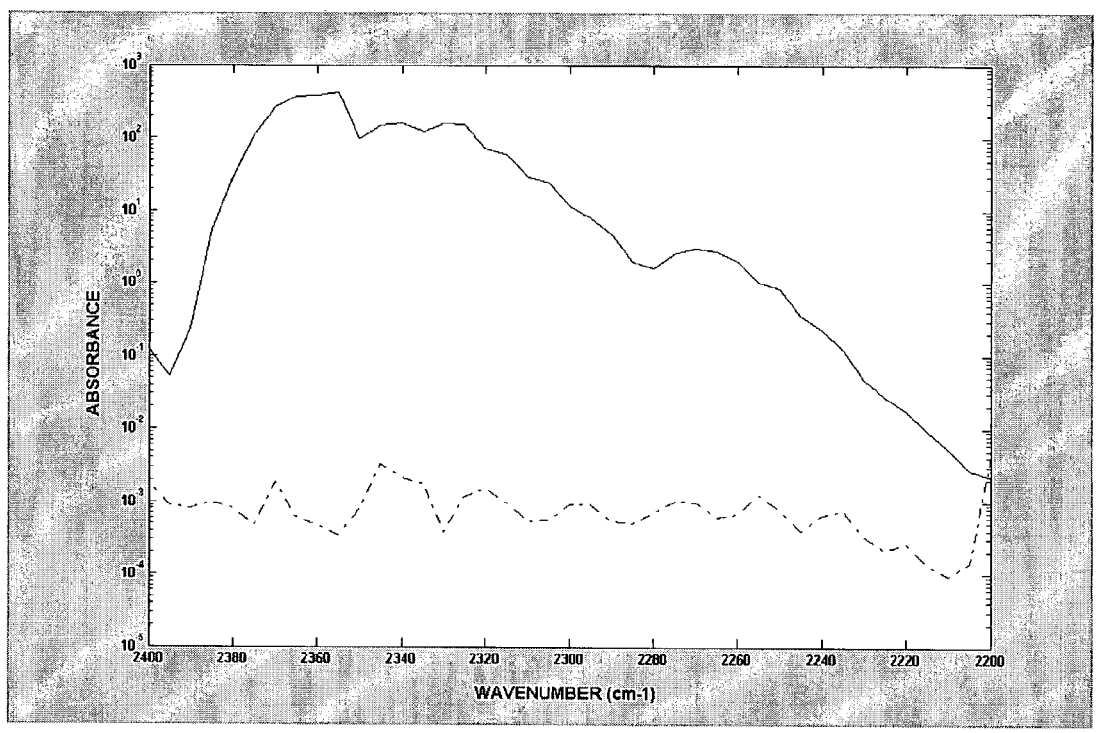
FIG. 10 shows a comparison of the absorbance of $CO_2$ and $CH_4$ over the spectral range 2400–2240 $cm^{-1}$ ($\lambda$=4.17–4.46 $\mu$m) for the gas concentrations $C_G(CO_2)$=0.84 moles per liter and $C_G(CH_4)$=10.82 moles per liter and an optical path length of $L_1$=3 mm.

For example, FIG. 10 shows a comparison of the absorbance (=ln($I_o/I$) from eqn. [12]) of $CO_2$ and $CH_4$ over the spectral range 2400–2200 cm$^{-1}$ ($\lambda$=4.17–4.42 $\mu$m) for the gas concentrations determined in the $CO_2$ detection example above ($C_G(CO_2)$=0.84 moles per liter; $C_G(CH_4)$=10.82 moles per liter) for an optical path length of $L_1$=3 mm. The methane contributes less than 0.01% of the total absorbance in the spectral range 2380–2320 cm$^{-1}$ ($\lambda$=4.20–4.31 $\mu$m). In comparison, the methane contributes 1% of the total absorbance at 2220 cm$^{-1}$ ($\lambda$=4.50 $\mu$m).

Thus the accurate determination of the concentration of $CO_2$ in $CH_4$ depends on the relative concentrations of the two components and the choice of spectral region over which the measurement is made. For example, at low concentrations of $CO_2$ and high concentrations of $CH_4$ the spectral region 2380–2320 cm$^{-1}$ ($\lambda$=4.20–4.31 $\mu$m) is most suitable, while for high concentrations of $CO_2$ and low concentrations of $CH_4$ the spectral region 2250–2200 cm$^{-1}$ ($\lambda$=4.44–4.55 $\mu$m) is more appropriate. Alternatively, the absorbance due to $CH_4$ in the spectral region 2400–2240 cm$^{-1}$ ($\lambda$=4.17–4.46 $\mu$m) can be corrected by the use of a second LED operating in the spectral region 3075–2985 cm$^{-1}$ ($\lambda$=3.25–3.35 $\mu$m).

Influence of Liquid Water and Liquid Hydrocarbons on Gas

Figure 11:
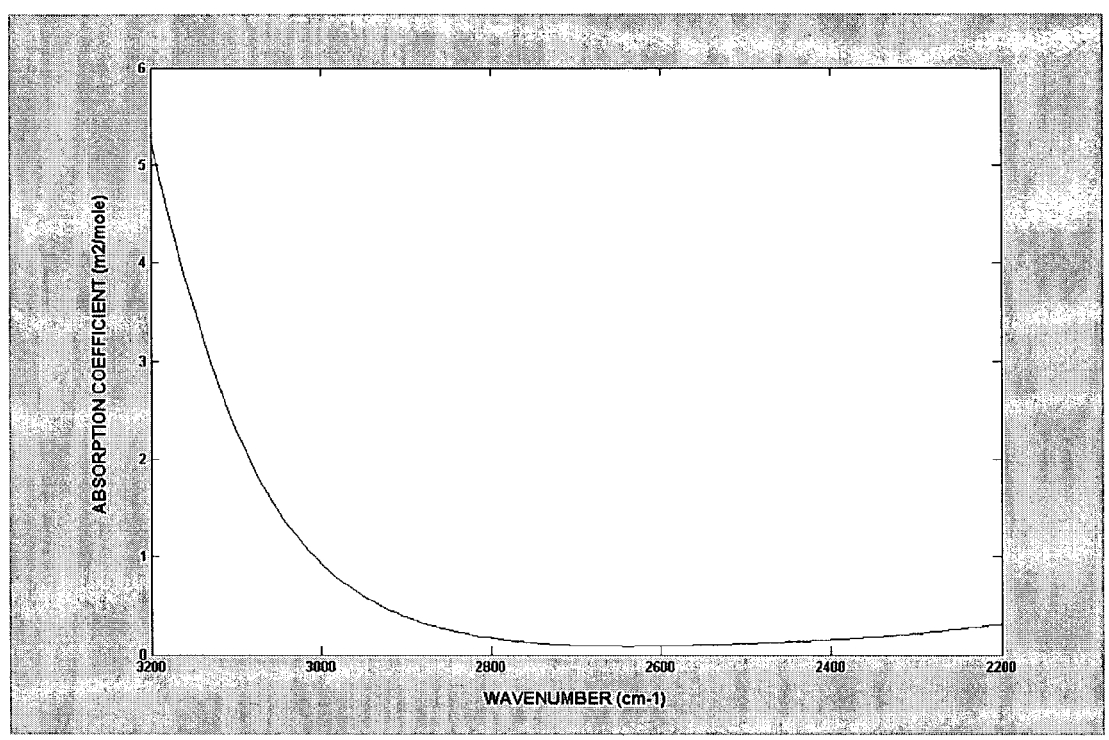
FIG. 11 shows the dependence of the absorption coefficient $\epsilon$ of liquid water on wavelength at ambient temperature over the wavenumber range 3200–2200 $cm^{-1}$ ($\lambda$=3.13–4.55 $\mu$m)

Detection and Quantification The presence of thin films or droplets of water or oil in the optical path $L_1$ of the LED gas sensor can significantly contribute to the absorbance measured by detector D1 and hence determination of gas concentrations. FIG. 11 shows the dependence of the absorption coefficient $\epsilon$ of liquid water on wavelength at ambient temperature over the wavenumber range 3200–2200 cm$^{-1}$ ($\lambda$=3.13–4.55 $\mu$m, resolution of data is 8 cm$^{-1}$) (50). Over the spectral range 2400–2250 cm$^{-1}$ the average value of $\epsilon$ for bulk water is 0.2 m$^2$/mole, which is three orders of magnitude less than the peak value of $\epsilon$ for $CO_2$ at 2360 cm$^{-1}$.

However, the molar concentration of bulk water is 55,556 moles/m$^3$, which is a considerably larger concentration than that expected for $CO_2$ or $CH_4$ in wellbore gas samples. From eqn. [13], with $\epsilon$=0.2 m$^2$/mole and C=55,556 mole/m$^3$, the maximum value of the optical path L in bulk water is 0.27 mm.

A similar situation occurs with liquid hydrocarbons where, for a mean molecular weight of 0.226 kilograms per mole (hydrocarbon distribution centred on $C_{16}$) and a density of 780 kilograms/m$^3$, the molar concentration is 3450 moles/m$^3$. This concentration of $C_{16}H_{34}$ equates to a concentration of —$CH_2$— groups of 55,200 moles/m$^3$, which is similar to the concentration of $H_2O$ in bulk water.

Figure 12:
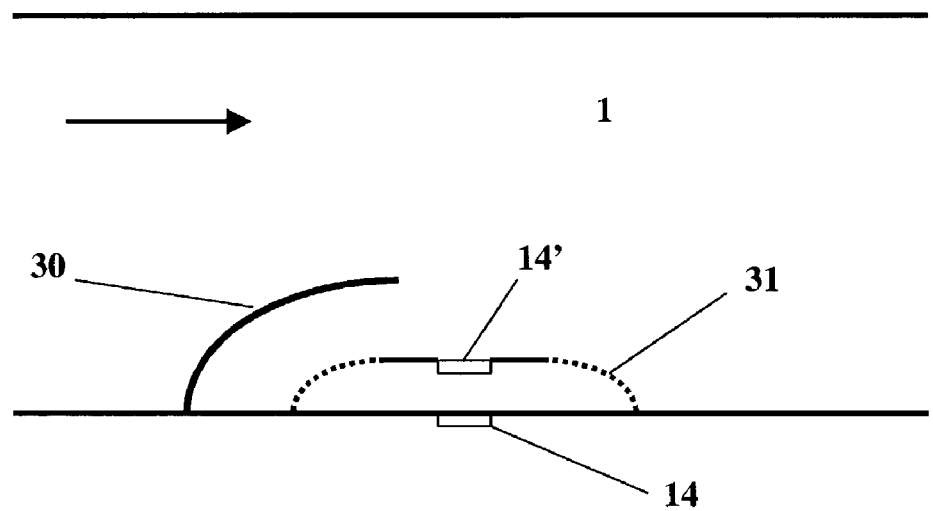
FIG. 12 shows a schematic diagram of a shield and a coarse filter arranged in a flow line to protect a gas sensor from the direct impact of liquid droplets.
Figure 13:
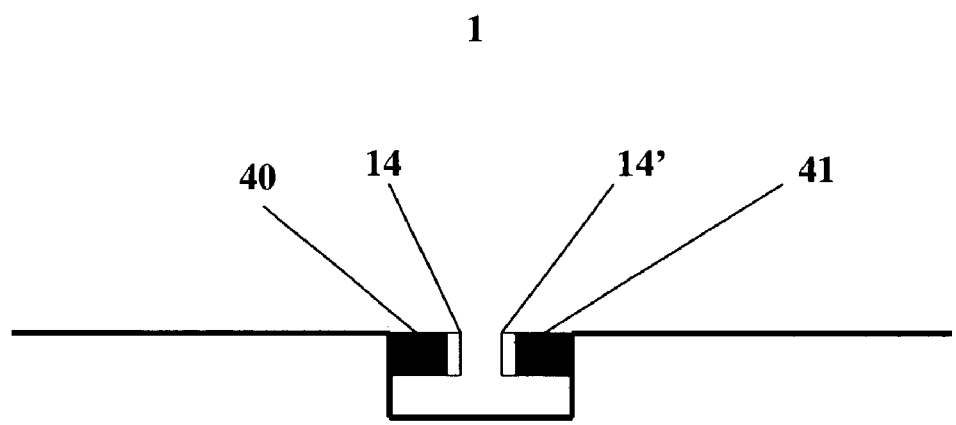
FIG. 13 shows a schematic diagram of a gas sensor comprising acoustic horns.

Thus in a practical design of a gas sensor using mid-infrared radiation for spectral detection, the optical path length $L_1$ should be substantially free of water and hydrocarbon in their liquid states. The design and operation of a gas sensor using mid-infrared LEDs and photodiodes will therefore generally require the use of a filter to remove water and oil droplets from the gas stream or gas sample as described above in relation to the sensor configurations of FIGS. 2, 4 and 6. However, further protection may be provided. FIG. 12 shows schematically optical windows 14, 14' which respectively cover the LED and detector D1 and of a gas sensor mounted in flow line 1, the sensor being protected from the direct impact of liquid droplets by a combination of a shield 30 and a coarse filter 31. The arrow indicates the direction of flow in the flow line. The filter 31 may be heatable to prevent the accumulation of liquid on the filter surface and penetration to the LED optics. FIG. 13 shows an alternative design to prevent the deposition of liquid onto the optics of a gas sensor. The LED and photodiode detector D1 are covered by respective optical windows 14, 14', and are located in small acoustic horns 40, 41 set into the wall of the flow line 1 or sample chamber. The acoustic horns, which may be operated at elevated temperatures and pressures at frequencies up to 150 kHz (see e.g. WO 01/31328), can be periodically activated to generate high power ultrasound to remove liquid films from the optical window.

LED Operation

The LED of the gas sensor can be operated in one of several modes. It is preferable to operate the LED in a pulse mode where the duty cycle is typically in the range 0.1–10%, thus reducing Joule heating effects. Pulse widths are typically in the range of time interval 10–1000 $\mu$s with a pulsing frequency in the range 100–1000 Hz. A further advantage of pulsing is that the output signal of the detector can be averaged over a large number of measurements, thus improving the signal-to-noise ratio.

At elevated temperatures it may be advantageous to operate the LED in so-called negative luminescence mode, i.e. the LED is operated under reverse bias conditions and the LED becomes a net absorber of infrared radiation. The quantum efficiency of mid-infrared LEDs can be higher when operated under reverse bias conditions than under normal bias at elevated temperatures, thus raising the value of the absorptive power of the LED and increasing the signal, albeit negative, measured by the detector. The presence of an absorbing gas in the optical path between the LED operating in negative luminescence mode and the photodiode detector results in a less negative signal being measured by the detector. The Beer-Lambert law, as for example expressed in eqn. [12], is applicable when the LED is operated under reverse bias conditions with both I and $I_o$ being negative.

Gas Sensing by Internal Reflection Measurements

Figure 14:
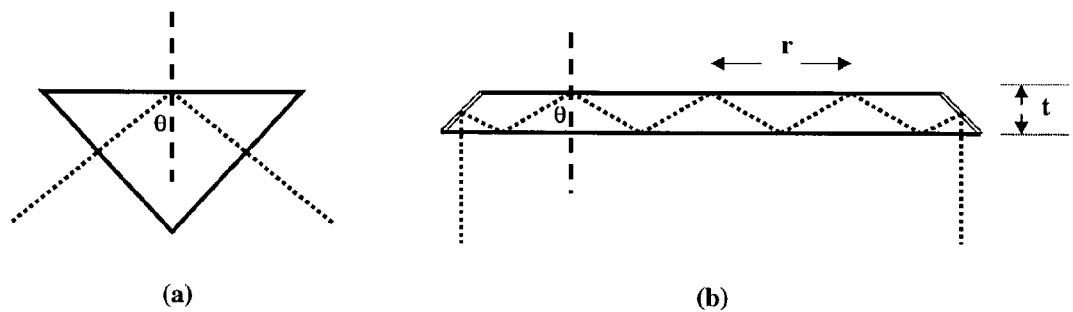
FIGS. 14a and b show respective schematic diagrams of single and multiple internal reflection elements.

The LED-based gas sensor configurations described above determine the concentration of gaseous components by transmission of infrared radiation along an optical path length $L_1$ of order 1 mm. An alternative approach is to determine the concentration by an internal reflection method whereby the optical path length $L_1 < \lambda$. FIGS. 14$a$ and $b$ show respective schematic diagrams of single and multiple internal reflection elements, the dashed lines indicating typical optical paths. Total internal reflection of the infrared radiation is accompanied by the propagation of an evanescent wave into the optically rarer medium (i.e. the surrounding gas). The evanescent wave decays exponentially into the optically less dense medium and the characteristic decay length $D_T$, frequently termed the penetration depth, is given by (51)

$$D_T = \frac{\lambda}{2\pi[n_1^2 \sin^2\theta - n_2^2]^{1/2}} \quad [14]$$

where $n_1$ and $n_2$ are the respective refractive indices of the optically denser (crystal) and rarer (gas) phases ($n_1 > n_2$), and $\theta$ is the angle of incidence made by the infrared radiation at the crystal-gas interface (see FIG. 14).

The refractive index $n_2$ of the gaseous phase can be estimated from the Lorentz-Lorenz equation (52, 53)

$$\frac{n_2^2 - 1}{n_2^2 + 2} = \frac{R_o}{V_m} \quad [15]$$

where $R_o$ is the molar refraction of the component and $V_m$ is its partial molar volume. The molar refraction of $CH_4$ is reported in the range $6.36 \times 10^6$ m$^3$/mole (53) to $6.86 \times 10^{-6}$ m$^3$/mole (52) and $V_m$ is a function of the temperature and pressure of the gas ($=RT/P_i$ for an ideal gas). For the $CH_4$ detection example given above, a methane concentration of 13.13 moles per liter yields a molar volume of $V^m = 7.62 \times 10^{-5}$ m$^3$/mole, whereupon eqn. [15] gives $n_2 = 1.13$ with an average value of Ro of $6.61 \times 10^{-6}$ m$^3$/mole. If the internal reflection crystal is taken to be sapphire with a refractive index $n_1 = 1.70$ at $\lambda 3.3$ μm (46) and a value of $\theta = 45°$, eqn. [14] yields $D_T = \lambda/2.4 = 1.38$ μm. With $L_1 = 1.38$ μm, eqn. [12] predicts that the photodiode detector signal changes from 0.218 mV to 0.217 mV. However, a larger difference in signal can be achieved with multiple reflections (FIG. 14$b$). The distance r between reflections is 2ttan$\theta$, where t is the thickness of the optical crystal. With t=1 mm and $\theta = 45°$, r=2 mm giving 10 reflections in an optical window 20 mm in length and a corresponding change in the signal of detector D1 from 0.218 to 0.213 mV. Yet larger changes in the signal from D1 can be achieved by increasing the number of reflections (e.g. decreasing the thickness t of the optical window) or operating the measurement close to the critical angle $\theta_c$ ($=\sin^{-1}(n_2/n_1)$). For example, decreasing the window thickness to t=100 μm, with the window supported on a silvered metal substrate, gives 5 reflections per millimeter of window with $\theta = 45°$. An optical window 20 mm in length gives 100 reflections with a total optical path length of 0.14 mm and the corresponding signal of detector D1 changes from 0.218 mV to 0.172 mV.

In contrast, $CO_2$ can be detected by a single reflection when the output of the LED is filtered to operate in the spectral region 2380–2320 cm$^{-1}$ ($\lambda = 4.20$–4.31 μm). For example, in the example of $CO_2$ quantification given above, with $C_G = 0.84$ moles per liter, an average value of the molar absorption coefficient $\epsilon$ of 200 m$^2$/mole and a penetration depth $D_T$ of 1.14 μm (from eqn. [14] with $n_1 = 1.70$, $n_2 = 1.10$, $\theta = 45°$ and $\lambda = 4.24$ μm), the absorbance due to one reflection is 0.24. This value of absorbance is readily measured by the photodiode detector.

An important aspect of internal reflection spectroscopy is that the penetration depth $D_T$ depends on the refractive index $n_2$ of the analyte (optically less dense) phase and hence its composition. In the case of detecting $CO_2$ in $CH_4$, the value of $n_2$ will depend on the effective value of $R_o/V_m$ for the mixture. Fortuitously, the values of $R_o$ for $CH_4$ and $CO_2$ are almost identical with $R_o$ for $CO_2$ being $6.59 \times 10^{-6}$ m$^3$/mole (52, 53). The value of $D_T$ can therefore be determined from eqn. [15] with a value of $R_o$ of $6.6 \times 10^{-6}$ m$^3$/mole and a value of $V_m$ estimated from ideal gas behaviour using the measured value of gas pressure. Further refinement in the value of $V_m$ can be made by iteration using an appropriate equation of state starting with the approximate value of the concentrations of $CO_2$ and $CH_4$.

One feature of an optical sensor that determines gas concentration using internal reflection is that under certain circumstances the sensor can discriminate the formation of liquid films on the optical window. For example, in the case of the $CH_4$ detection example with a $CH_4$ concentration of 13.13 moles per liter, the molar volume is $7.62 \times 10^{-5}$ m$^3$/mole and eqn. [15] predicts the refractive index $n_2 = 1.14$. The refractive index of a sapphire window at $\lambda = 3.3$ μm is $n_1 = 1.70$ and $\theta = 42.10$. The condition $\theta > 42.10$ results in the infrared radiation being total internally reflected in the sapphire crystal. If, however, water is deposited on the sapphire crystal, $\theta_c$ will increase to 51.50 since $n_2$ has increased to 1.33. If $\theta$ is less than 51.50, then the infrared radiation will propagate into the water and no signal will be received by the detector. The value of $\theta$ can thus be chosen to be close to $\theta_c$ for the sapphire-water interface to enable total internal reflection to be achieved for the largest possible gas density. When the density of $CH_4$ gas is 476 grams per liter ($V_m = 3.36 \times 10^5$ m$^3$/mole), its refractive index reaches that of water and no discrimination can be made between the two phases using total internal reflection.

Wireline Sampling Tool

The gas sensor can be used on a wireline sampling tool, such as Schlumberger's Modular Dynamics Testing Tool (MDT) (45), commonly used in the exploration wells to appraise hydrocarbon-bearing formations. The sensor can be used directly in a flow line to measure the concentration of $CO_2$ or $CH_4$ or other gas of interest in gas samples captured by the sampling tool. Alternatively, the sensor can be used to measure the concentration of specific gases in the headspace above a liquid sample, as described in WO 01/63094. In the latter case the concentration of the component in the headspace sample can be used with Henry's Law to establish the concentration of the component in the original liquid phase.

Production Logging Tool

It is frequently desirable to intervene in producing wells to determine the flow rate of the various phases (liquid hydrocarbon, gas and water) under the particular production conditions. Considerably less common is the determination of the composition of the fluid phases.

Figure 15:
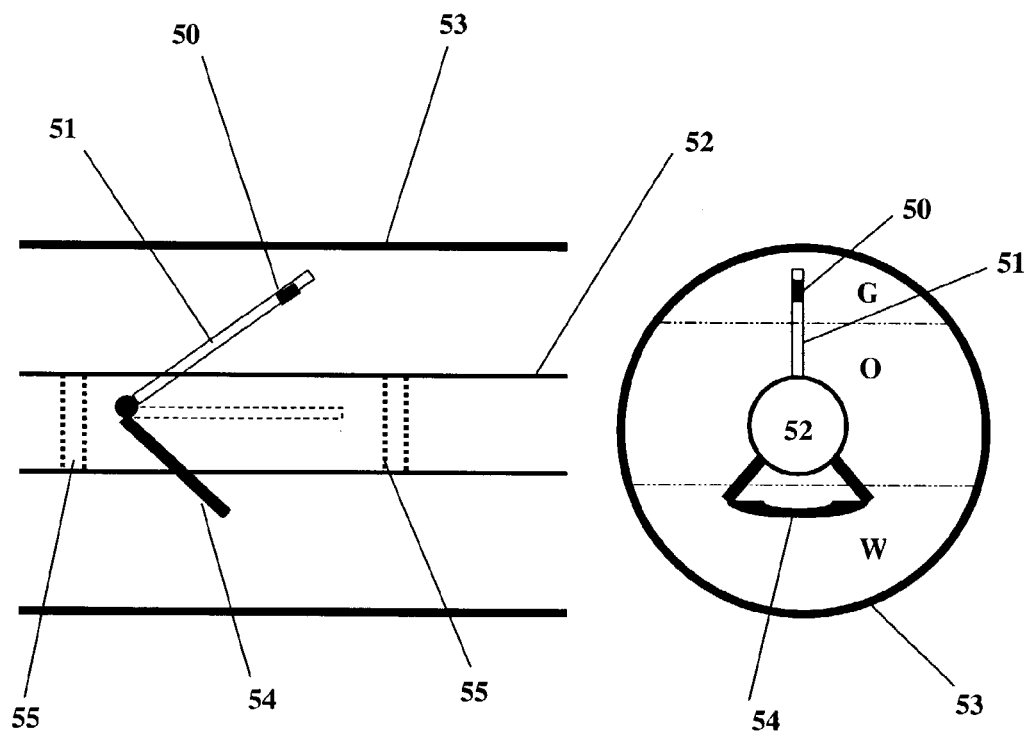
FIG. 15 shows schematic diagrams of longitudinal and transverse sections through a production logging tool fitted with an LED-based gas sensor.

However, the concentration of certain components, such as $CO_2$ and $CH_4$, in the produced gas phase can be determined using a mid-infrared LED gas sensor. FIG. 15 shows longitudinal and transverse sections of a production logging tool fitted with an LED-based gas sensor and positioned in a horizontal well 53. The LED gas sensor 50 (e.g. having the configuration of FIG. 2, 4 or 6 described above) is mounted on a retractable arm 51, which is connected to the central body 52 of the production logging tool. The fluid flow is stratified into gas G, oil O and water W phases. When the measurement is to be made the arm 51 is extended upwards into the gas phase. Simultaneously a lower weighting arm 54 is extended. The portion of the tool connected to the arms is unlocked to allow it to rotate freely about bearings 55, but the weighting arm serves to keep the sensor in the gas phase.

Figure 16:
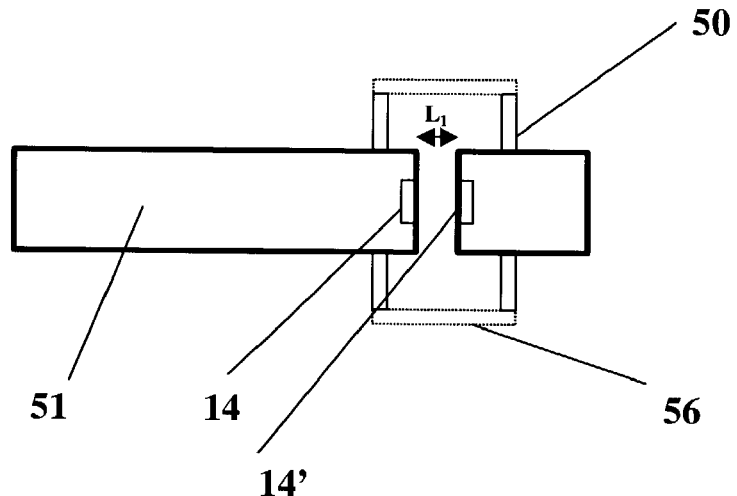
FIG. 16 shows a schematic diagram of the gas sensor of FIG. 15.

FIG. 16 shows a schematic diagram of the LED gas sensor 50 on the retractable arm 51 of the production logging tool.

The optical windows 14, 14' that define the optical path length $L_1$ can be protected from particulate material and liquid droplets by means of a filter 56. Furthermore, liquid films can be removed from the optical windows when the sensor is immersed in the gas phase by incorporating the LED and detector into a small high power ultrasonic transducer. Increases in the value of the signal $I_1$, when the transducer has been operated in the gas phase would indicate the removal of liquid films from the optical windows.

Measurement While Drilling

The detection of gases such as $H_2S$ and $CH_4$ in the circulating drilling fluid at the surface during drilling operations is routine. Typically the concentration of $CH_4$ and other hydrocarbon gases is determined using gas chromatography, while the concentration of $H_2S$ can be determined using a metal oxide gas sensor. However, the concentration of the gaseous species in the drilling fluid is generally determined at the surface approximately 1–2 hours after they entered the wellbore. It would be advantageous to detect rapidly the influx of the gas at the point of entry, and before the gas has reached the surface. For example, the in situ detection of $CH_4$ may give early warning of a gas kick.

Figure 17:
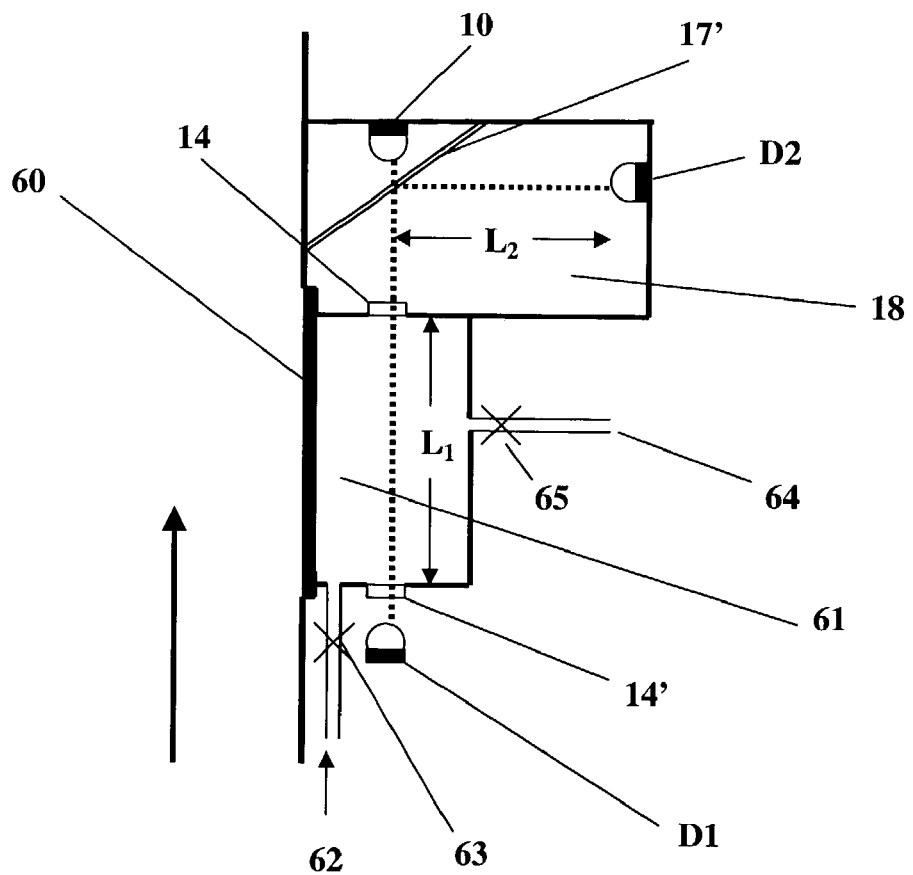
FIG. 17 shows a schematic diagram of a $CH_4$ sensor on the bottom hole assembly of a drill string.

FIG. 17 shows a schematic diagram of a $CH_4$ sensor on the bottom hole assembly of a drill string. The arrow indicates the direction of flow of the drilling fluid. The sensor comprises a thin membrane 60 made of a material, such as a polymer or zeolite, in the form of a thin film (10–100 μm) on a supporting porous substrate. Alternatively, the membrane can be formed of an inert porous material saturated with a fluorinated polyether in which gases such as $CH_4$, $CO_2$ and $H_2S$ are highly soluble but in which neither liquid hydrocarbons nor water are soluble (see e.g. U.S. Pat. No. 6,037,592). The membrane allows the transport of $CH_4$ and other gases but prevents the movement of water and liquid hydrocarbon into gas analysis chamber 61. Similar membranes have been described in WO 01/63094 for the analysis of $H_2S$ using optical, electrochemical and other chemical sensors.

The sensor has an LED 10, detectors D1 and D2, optical window 14, beam splitter 17' and reference gas compartment 18 arranged according to the sensor configuration of FIG. 4. A further optical window 14' protects detector D1. The dashed lines indicates the optical paths. Length $L_1$ of the optical path between the LED and detector D1 traverses gas analysis chamber 61.

The concentration $C_m$ of the gas component in the drilling fluid can be determined either from a measurement of the flux of the gas species across membrane 60 or when equilibrium has been achieved between the gas component in the drilling fluid and the analysis chamber. The case of equilibrium being reached between the gas in the drilling fluid and the reaction chamber is similar to a headspace measurement, albeit the gas and liquid phases being separated by a membrane. Equilibrium is achieved when the chemical potential of the gas component in the drilling fluid is equal to the chemical potential of the gas in the analysis chamber. At low gas concentrations in the drilling fluid, the partial pressure $P_i$ of the gas component in the analysis chamber is related to the mole fraction $X_i^m$ of the gas in the drilling fluid by Henry's law:

$$P_i = HX_i^m \quad [16]$$

where H is the Henry's law constant for the particular gas and drilling fluid. The mole fraction $X_i^m$ of the gas in the drilling fluid is defined by $$X_i^m = \frac{n_i^m}{n_i^m + n_s} \quad [17]$$

where $n_i^m$ is the number of moles of gas in $n_s$ moles of drilling fluid. In the case of a dilute solution of the gas in the liquid, $n_i^m << n_s$ and $$X_i^m \approx \frac{n_i^m}{n_s} = \frac{c_i^m \overline{M}_w^s}{\rho_s} = \frac{c_i^m \overline{M}_w^s}{M_{wi}\rho_s} \quad [18]$$

where $c_i^m$ is the molar concentration of the gas in the drilling fluid, $C_i^m$ is the mass concentration of the gas in the drilling fluid, $\overline{M}_w^s$ is the average molecular weight of the drilling fluid, $\rho_s$ is its density and $M_{wi}$ is the molecular weight of the gas.

The pressure $P_i$ of the gas in the analysis chamber is determined by the LED gas sensor via a concentration measurement. In the case of a low value of $P_i$ (typically less than 100 bar) and high temperatures (typically in excess of 100° C.), the gas behaves approximately as an ideal gas and Pi is related to the measured molar gas concentration $c_i^g$ by $$c_i^g = \frac{P_i}{RT} = \frac{HX_i^m}{RT} \approx \frac{Hc_i^m \overline{M}_w^s}{\rho_s RT} \quad [19]$$

and therefore $$c_i^m \approx \frac{c_i^g \rho_s RT}{H \overline{M}_w^s} \quad [20]$$

The concentration $c_i^g$ of the gas in the analysis chamber is obtained from the Beer-Lambert law using the LED gas detector with a known value of $\varepsilon_i$:

$$c_i^g = \frac{A}{\varepsilon_i L_1} \quad [21]$$

The value of the Henry's law constant for the solubility of methane gas in n-alkanes depends little on hydrocarbon chain length and is relatively insensitive to hydrocarbon type (diesel, olefin, mineral and ester oils) (54). For example, the Henry's law constant for n-alkanes in the range $C_5$–$C_{20}$ at a temperature of 100° C. is 270 bar (54).

An example of the sensitivity of the sensor can now be given. A mineral oil drilling fluid at 100° C. contains $CH_4$ gas at a concentration of 2.8 kg/M³. The average molecular weight $\overline{M}_w{}^s$ of the mineral oil is 0.226 kg/mole (hydrocarbon distribution centred on $C_{16}$) and its density is 800 kg/m³. The mole fraction $X_i{}^m$ of the gas in the mineral oil is 0.05, which from eqn. [16] with H=270 bar, yields a partial pressure in the gas analysis chamber of 13.5 bar. Assuming the $CH_4$ gas in the analysis chamber acts as an ideal gas, the gas phase concentration in the chamber is $c_i{}^g\mu$=441 mole/m³. The absorbance measured in the LED gas sensor is A=0.57 for an optical path length $L_1$=1 cm and $\epsilon_i$=0.13 m²/mole for the spectral range λ=3.12–3.57 µm.

The measurement of gas concentration under equilibrium conditions can be determined by one of several methods. The simplest method is to allow the gas concentration in the analysis chamber to be determined entirely by the concentration of the gas in the drilling fluid. When the concentration $C_i{}^m$ of the gas in the drilling fluid increases, the gas diffuses into the analysis chamber and $P_i$ and $c_i{}^g$ increase. Conversely, when $C_i{}^m$ decreases, gas diffuses out of the chamber and $P_i$ and $c_i{}^g$ decrease. Clearly a rapid response time for the sensor is required, which can be achieved by a thin membrane with a high diffusivity for the gas and a chamber of small volume. Alternatively, the gas in the chamber can be removed by flowing an inert (non-absorbing) gas, such as dry nitrogen, into the chamber. In the sensor of FIG. 17 nitrogen can be introduced via inlet 62 and valve 63, and pumped or vented out via outlet 64 and valve 65. The active removal of wellbore gas from the sensor may decrease the response time of the sensor.

The gas sensor can also be operated in a dynamic mode where the gas in the analysis chamber does not reach equilibrium with the gas in the drilling fluid. If the total gas pressure in the analysis chamber is low and the width of the chamber is small, then it can be assumed that the concentration of the gas in the chamber is uniform. The concentration of gas in the drilling fluid can be determined by the rate of change of concentration in the chamber as determined by the rate of change of absorbance. The equilibrium gas concentration $c_i{}^g$, as given by eqn. [19], can be calculated from $$c_i^g = \frac{c_{it}^g - c_{io}^g e^{-\alpha t}}{1 - e^{-\alpha t}} \quad [22]$$

where $c_{io}{}^g$ is the molar concentration of gas in the chamber at the start of the analysis (e.g. the residual gas concentration), $c_{it}{}^g$ is the molar gas concentration in the chamber after time t and the constant α is given by $$\alpha = \frac{S_m D}{LV} \quad [23]$$

where $S_m$ is the cross-sectional area of the membrane, D is the diffusion coefficient of the analyte gas in the membrane, L is the thickness of the membrane and V is the volume of the analysis chamber. The time τ=1/α is the characteristic response time of the gas sensor. The concentrations $c_{io}{}^g$ and $c_{it}{}^g$ are measured by the LED gas sensor, $c_i{}^g$ is determined by eqn. [22] and the concentration $c_i{}^m$ of gas in the drilling fluid is calculated using eqn. [20].

The LED gas sensor can also be operated under dynamic conditions using a constant flow of an inert gas, such as nitrogen, to flush the diffusing gas into the analysis cell. The molar flow rate Q of nitrogen flushing the membrane maintains the concentration of the diffusing gas at zero such that the molar flux $J_i$ of gas across the membrane is $$J_i = \frac{Dc_i^g S_m}{L} \quad [24]$$

where $c_i{}^g$ is related to $c_i{}^m$ by eqn. [20]. The molar concentration $c_{if}{}^g$ of analyte gas in the nitrogen stream is $$c_{if}^g = \frac{J_i}{Q} = \frac{Dc_i^g S_m}{QL} \quad [25]$$

and therefore $c_i{}^g$ is given by $$c_i^g = \frac{c_{if}^g QL}{DS_m} \quad [26]$$

The concentration $c_{if}{}^g$ of analyte gas in the nitrogen stream is determined by the LED gas sensor using eqn. [21] with known values of $\epsilon_i$ and $L_1$.

Permanent Monitoring

It may be advantageous to locate a gas sensor in a producing or observation well over an extended time period in order to detect changes in gas composition. For example, an LED gas sensor with a gas extraction membrane, similar in configuration to that shown in FIG. 17, can be located on completion in a producing well to monitor the concentration of gases, such as $CO_2$ and $CH_4$, in the produced fluids. A similar gas sensor can be placed in an observation well placed above the seal of a reservoir used to store $CO_2$ in order to monitor gas leakage through the seal.

Reactive $H_2S$ Sensor

An alternative method of measuring the concentration of hydrogen sulfide using mid-infrared spectroscopy is by the detection of sulfur dioxide ($SO_2$) after oxidation by some suitable reaction. Larsen et al. (64) have described the oxidation of $H_2S$ to $SO_2$ using ultraviolet light and air and subsequent detection of the $SO_2$ using mid-infrared spectroscopy. The fundamental S=O stretching bands are in the spectral region 1400–1050 cm⁻¹ (7.1–9.5 µm) with the most intense band located at 1350 cm⁻¹ (7.4 µm). For example, the $H_2S$ can be oxidised to $SO_2$ using air from a source of compressed air on the downhole tool either with a porous, catalytic membrane, such as cerium oxide (65), or with ultraviolet light. The water produced by the oxidation of the $H_2S$ to form $SO_2$ can be removed by the use of a suitable water scavenger in the form of a packed bed, such as a molecular sieve or an anhydrous salt, e.g., calcium chloride.

Figure 18:
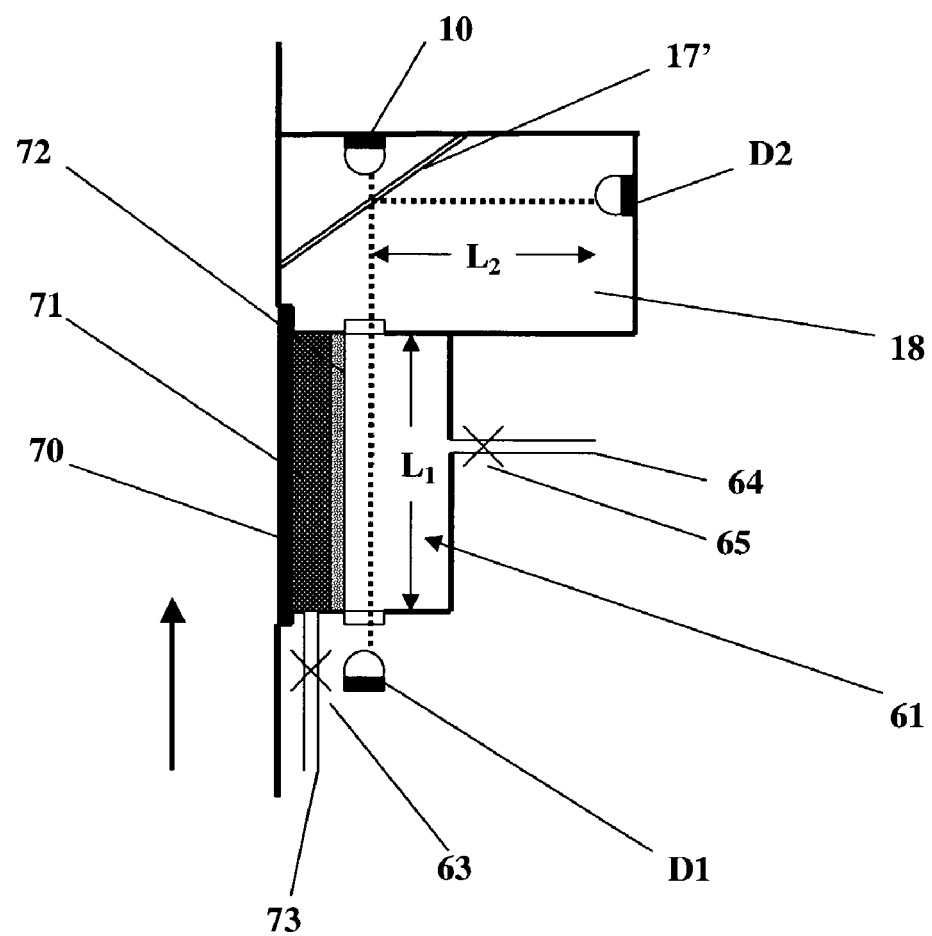
FIG. 18 shows a schematic diagram of a reactive $H_2S$ sensor on the bottom hole assembly of a drill string.

FIG. 18 shows a schematic of an $H_2S$ sensor that comprises a gas stripping membrane 70 to remove $H_2S$ from the wellbore, a catalytic membrane 71 flushed with air from the compressed air source 73 to oxidise it to $SO_2$, a porous bed 72 of a desiccant to remove water from the oxidised gas stream and a gas analysis chamber 61 to measure the concentration of the $SO_2$ generated. Effectively, thin membrane 60 in the sensor of FIG. 17 is replaced by gas stripping membrane 70, catalytic membrane 71 and a porous dessicant bed 72. The temperature of the catalytic membrane may have to be raised to several hundred degrees centigrade above ambient temperature to ensure that efficient conversion of $H_2S$ to $SO_2$ is achieved. The elevated temperature may be achieved by the incorporation of a small heating element in the catalytic membrane. Such an element may be sandwiched between thin thermal insulator layers but should maintain permeability to $H_2S$ and $SO_2$. The pressure of the compressed air in the gas sensor and its flow rate through the sensor are controlled by the valve 63 and choke 65. The concentration of $SO_2$ in the air stream is given by eqn. [25], noting that the molar flow rate of oxygen in the stream must be sufficient to oxidise the $H_2S$ diffusing across the membrane. The $SO_2$ generated by the oxidation of $H_2S$ is removed from the cell through a vent 64.

The reactive $H_2S$ sensor further comprises an LED 10, detector D1 and a reference compartment 18 containing $SO_2$ at a known concentration and detector D2. By way of example, the response of the sensor to a gas stream containing 8.1 grams of $H_2S$ per liter of gas (methane) at a temperature of 140° C. and a pressure of 6150 psi (418 bar) can be determined. The diffusivity D of $H_2S$ through the separation membrane 70 (which has an area of $10^{-2}$ m$^2$ and a thickness of 50 µm) is $9.2 \times 10^{-11}$ m$^2$/s, the $H_2S$ being flushed from the inner surface of the separation membrane by the flow of air. From the condition of an $H_2S$ concentration of zero on the inner surface of the separation membrane, eqn. [24] gives the flux J of $H_2S$ through the separation membrane to be $4.4 \times 10^{-6}$ moles per second. The pressure of the air in the catalytic membrane 71 is 588 psi (40 bar), which, assuming the air behaves as an ideal gas, gives an oxygen concentration of 0.236 moles per liter. The flow rate Q of the air through the catalytic membrane is 3 cm$^3$ per minute ($5 \times 10^{-8}$ m$^3$/s) and from eqn. [25] the concentration of $SO_2$ emerging into the gas detection chamber 61 is 0.088 moles per liter of gas. The optical path length $L_1$ of the gas detection chamber is 10 cm and the absorption coefficient $\epsilon$ of $SO_2$ is 0.052 m$^2$/mole at a wavelength of $\lambda=7.25$ µm, from which values an absorbance of 0.46 is obtained. The sensitivity of the detector can be modified by changing either the flux J of $H_2S$ across the separation membrane 70 (e.g., the thickness of the membrane) or the flow rate Q of the air in the catalytic membrane 71.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

REFERENCES

All references mentioned below or in the above text are incorporated by reference.

1. Biefeld, R. M., Allerman, A. A. and Kurtz, S. R., "Recent advances in mid-infrared (3–6 µm) emitters", *Materials Science Engineering*, B51, 1–8 (1998); Allerman, A. A., Kurtz, S. R., Biefeld, K. C., Baucom, K. C. and Burkhart, J. H., "Development of InAsSb-based light emitting diodes for chemical sensing systems", *SPIE*, 3279, 126–133 (1998).
2. Kost, A. R., "Materials for mid-infrared semiconductor lasers", *Mat. Res. Soc. Symp.*, 484, 3–10 (1998).
3. Aidaraliev, M., Zotova, N. V., Karandashev, S. A., Matveev, B. A., Remennyi, M. A., Stus', N. M. and Talalakin, G. N., "Light emitting diodes for the spectral range λ=3.3–4.3 µm fabricated from the InGaAs and InAsSbP-based solid solutions: electroluminescence in the temperature range 20–180° C.", *Semiconductors*, 34, 104–107 (2000); Aidaraliev, M., Zotova, N. V., Karandashev, S. A., Matveev, B. A., Remennyi, M. A., Stus', N. M. and Talalakin, G. N., "Light emitting diodes for the spectral range λ=3.3–4.3 µm fabricated from InGaAs and InAsSbP solid solutions: electroluminescence in the temperature range 20–180° C. (part 2)", *Semiconductors*, 35, 598–604 (2001).
4. Ashley, T., "Type-I InSb-based mid-infrared diode lasers", *Phil. Trans. R, Soc. Lond. A*. 359, 475–488 (2001).
5. Krier, A., "Physics and technology of mid-infrared light emitting diodes", *Phil. Trans. R, Soc. Lond. A*. 359, 599–619 (2001).
6. Stradling, R. A., "Semiconductor light sources for infra-red applications: concluding remarks", *Phil. Trans. R, Soc. Lond. A*. 359, 645–658 (2001).
12. Popov, A. A., Stepanaov, M. V., Sherstnev, V. V. and Yakovlev, Y. P., "InAsSb light-emitting diodes for the detection of $CO_2$ (λ=4.3 µm)", *Tech. Phys. Lett.*, 24, 596–8 (1998).
13. Pullin, M. J., Hardaway, H. R., Heber, J. D., Phillips, C. C., Yuen, W. T. and Moeck, P., "Room-temperature InAsSb strained-layer superlattice light-emitting diodes at λ=4.2 µm with AlSb barriers for improved carrier confinement", *Appl. Phys. Lett.*, 74, 2384–2386 (1999).
14. Li, X., Heber, J., Pullin, M., Gevaux, D. and Phillips, C. C., "MBE growth of mid-infrared antimonide LEDs with strained electron barriers", *J. Crystal Growth*, 227–228, 600– 604 (2001).
15. Biefeld, R. M., Allerman, A. A., Kurtz, S. R. and Baucom, K. C., "Progress in the growth of mid-infrared InAsSb emitters by metal-organic chemical vapour deposition", *J. Crystal Growth*, 195, 356–362 (1998).
16. Smith, S. D., Crowder, J. G. and Hardaway, H. R., "Recent developments in the application of mid-infrared lasers, LEDs and other solid state sources to gas detection", *SPIE*, 4651, 157–172 (2002).
17. Krier, A. and Sherstnev, V. V., "Powerful interface light emitting diodes for methane gas detection", *J. Phys. D: Appl. Phys.*, 33, 101–106 (2000).
18. Matveev, B. A., Zotova, N. V., Karandashev, S. A., Remennyi, M. A., Stus', N. M. and Talalakin, G. N., "Backside illuminated In(Ga)As/InAsSbP DH photodiodes for methane sensing at 3.3 µm", *Proc. SPIE*, 4650, 173–178 (2002).
19. Gao, H. H., Krier, A., Sherstnev, V. and Yakovlev, Y., "InAsSb/InAsSbP light emitting diodes for the detection of CO and $CO_2$ at room temperature", *J. Phys. D: Appl. Phys.*, 32, 1768–1772 (1999).
20. Pullin, M. J., Hardaway, H. R., Heber, J. D. and Phillips, C. C., "Type-IT InAs/InAsSb strained-layer-superlattice negative luminescence devices", *Appl. Phys. Lett.*, 75, 3437–3439 (1999).
21. Elliott, C. T., "Negative luminescence and its applications", *Phil. Trans. R. Soc. Lon. A* 359, 567–579 (2001).
22. Olafsen, L. J., Vurgaftman, I., Bewley, W. W., Felix, C. L., Aifer, E. H., Meyer, J. R., Waterman, J. R. and Mason. W., "Negative luminescence from type-II InAs/GaSb superlattice photodiodes", *Appl. Phys. Lett.*, 74, 2681–2683 (1999).

23. Ashley, T., Gordon, N. T. and Phillips, T. J., "Optical modeling of cone concentrators for positive and negative IR emitters", *J. Mod. Optics,* 46, 1677–1696 (1999).

24. Welford, W. T. and Winston, R., *The Optics of Non-Imaging Concentrators*, pp. 1–6, Academic Press, New York (1978).

25. Ashley, T., Dutton, D. T., Elliott, N. T., Gordon, N. T. and Phillips, T. J., "Optical concentrators for light emitting diodes", *SPIE*, 3289, 43–50 (1998).

26. Matveev, B., Zotova, N., Karandashov, S., Remennyi, M., Il'inskaya, N., Stus', N., Shustov, V., Talalakin, G. and Malinen, J., "InAsSbP/InAs LEDs for the 3.3–5.5 μm spectral range", *IEE Proc.-Optoelectron.,* 145, 254–256 (1998).

27. Matveev, B. A., Zotova, N. V., Karandashev, S. A., Remennyi, M. A., Stus', N. M and Talalakin, G. N., "Towards longwave (5–6 μm) LED operation at 80° C.: injection or extraction of carriers?", *IEE Proc.-Optoelectron.,* 149, 33–35 (2002).

28. Jones, R. C., "Immersed radiation detectors", *Appl. Opt.,* 1, 607–613 (1962).

29. Smith, S. D., Vass, A., Karpushko, F., Hardaway, H. and Crowder, J. G., "The prospects of LEDs, diode detectors and negative luminescence in infrared sensing of gases and spectroscopy", *Phil. Trans. R. Soc. Lond. A,* 359, 621–634 (2001).

33. Matveev, B. A., Aydaraliev, M., Zotova, N. V., Karandashov, S. A., Remennyi, M. A., Stus', N. M., Talalakin, G. N., Malyutenko, V. K. and Malyutenko, O. Y., "Negative luminescence from InAsSbP diodes in the 4.0–4.3 μm range", *SPIE,* 4285, 109–116 (2001).

34. Crowder, J. G., Elliott, C. T. and Hardaway, H. R., "High performance, large area, uncooled detectors for mid-infrared wavelengths", *Electron. Lett.,* 37, 116–118 (2001).

35. Krier, A. and Mao, Y., "High performance uncooled InAsSbP/InGaAs photodiodes for the 1.8–3.4 μm wavelength range", *Infrared Physics & Technology,* 38, 397–403 (1997).

39. Krier, A., Sherstnev, V. V. and Gao, H. H., "A novel LED module for the detection of $H_2S$ at 3.8 μm", *J. Phys. D: Appl. Phys.,* 33, 1656–1661 (2000).

45. Schlumberger, *Wireline Formation Testing and Sampling*, Schlumberger Wireline and Testing, Houston (1996).

46. Harris, D. C., *Materials for Infrared Windows and Domes*, pp. 12–62, SPIE, Bellingham, Wash., USA (1999).

47. Phillips, W. J., "Band-model parameters of the 2.7-μm band of $H_2O$", *J. Quant. Spectrosc. Radiat. Transfer,* 43, 13–31 (1990); Phillips, W. J., "Band-model parameters for 4.3 μm $CO_2$ band in the 300–1000 K temperature region", *J. Quant. Spectrosc. Radiat. Transfer,* 48, 91–104 (1992).

48. Riedl, M. J., *Optical Design Fundamentals for Infrared Systems*, pp. 146–147, 2nd ed., SPIE Press, Bellingham Wash., USA (2001).

49. Strong, K., Taylor, F. W., Calcutt, S. B., Remedios, J. J. and Ballard, J., "Spectral parameters of self- and hydrogen-broadened methane from 2000 to 9500 $cm^{-1}$ for remote sounding of the atmosphere of Jupiter", *J. Quant. Spectrosc. Radiat. Transfer,* 50, 363–429 (1993).

50. Bertie, J. E. and Lan, Z., "Infrared intensities of liquids XX: the intensity of the OH stretching band of liquid water revisited, and the best current values of the optical constants of $H_2O(l)$ at 25° C. between 15,000 and 1 $cm^{-1}$", *Appl. Spectrosc.,* 50, 1047–1057 (1996).

51. Harrick, N. J., *Internal Reflection Spectroscopy*, pp. 27–33, John Wiley, New York (1967).

52. Moelwyn-Hughes, E. A., *Physical Chemistry*, pp. 372–375, Pergamon Press, London (1957).

53. Glasstone, S., *Textbook of Physical Chemistry*, 2nd edition, pp. 528–530, Macmillan, London (1956).

54. Berthezene, N., de Hemptinne, J.-C., Audibert, A. and Argiller, J.-F., "Methane solubility in synthetic oil-based drilling muds", *J. Pet. Sci. Tech.,* 23, 71–81 (1999).

61. Lechuga-Fossat, L., Flaud, J.-M., Camy-Peyret, C. and Johns, J. W. C., "The spectrum of natural hydrogen sulfide between 2150 and 2950 $cm^{-1}$", *Can. J. Phys.,* 62, 1889–1923 (1984).

62. Bykov, A. D., Naumenko, O. V., Smirnov, M. A., Sinista, L. N., Brown, L. R. Crisp, J. and Crisp, D., "The infrared spectrum of $H_2S$ from 1 to 5 μm", *Can. J. Phys.,* 72, 989–1000 (1994).

63. Håland, K., Barrufet, H. P., Rønningsen, H. P. and Meisingset, K. K., "An empirical correlation between reservoir temperature and the concentration of hydrogen sulfide", 1999 *SPE Int. Symp. Oilfield Chem.*, Houston, Tex., February 1999, SPE 50763.

64. Larsen, E. S., Hong, W. W. and Spartz, M. L., "Hydrogen sulfide detection by UV-assisted infrared spectrometry", *Appl. Spectrosc.,* 51, 1656–1667 (1997).

65. Peterson, D. R. and Winnick, J., "Utilization of Hydrogen Sulfide in an Intermediate-Temperature Ceria-Based Solid Oxide Fuel Cell", *J. Electrochem. Soc.,* 145, 1449–1453 (1998).

What is claimed is:

1. A method of monitoring gas in a downhole environment, comprising:
    providing downhole a mid-infrared light emitting diode;
    operating the diode to transmit respective infrared signals on a first optical path extending from the diode through a downhole gas sample and a second optical path extending from the diode through a reference gas sample;
    detecting the transmitted infrared signals;
    determining the concentration of a component of the downhole gas sample from the detected signals;
    wherein the first optical path is substantially free of water and hydrocarbon in their liquid states.

2. A method according to claim 1, wherein the light emitting diode is operated in forward bias.

3. A method according to claim 1, wherein the light emitting diode is operated in reverse bias.

4. A method according to claim 1, wherein the identified component is $CO_2$.

5. A method according to claim 1, wherein the identified component is $CH_4$.

6. A method according to claim 1, wherein the identified component is $H_2S$.

7. A method according to claim 1, wherein the light emitting diode has a room temperature peak emission wavelength in the range from 3 to 5 μm.

8. A method according to claim 1, wherein the reference gas sample comprises a predetermined concentration of said component.

9. A method according to claim 1, wherein the light emitting diode is operated to transmit a further infrared signal on a third optical path extending from the diode, the third optical path having a defined absorbance at the emission wavelength of the diode.

10. A method according to claim 9, wherein the defined absorbance is zero.

11. A method according to claim 1, wherein the length of the first optical path is adjusted or selected according to the expected concentration of said component.

12. A method according to claim 1, further comprising filtering the downhole gas sample to substantially remove liquids therefrom.

13. A method according to claim 1, wherein a plurality of mid-infrared light emitting diodes are provided, each diode being adapted for use in a respective temperature range, and the diodes are selectively operated according to the downhole temperature.

14. A method according to claim 1, wherein the first optical path comprises a waveguide which passes through the downhole gas sample, the infrared signal on the first optical path being transmitted along the waveguide by internal reflection.

15. A method according to claim 1, wherein a plurality of respective photodiode detectors are provided to detect the transmitted infrared signals.

16. A method according to claim 1, further comprising extracting the downhole gas sample through a gas extraction membrane to substantially remove liquids therefrom, the membrane allowing the transport of gases across it but preventing the transport of liquid water and hydrocarbon.

17. A sensor for monitoring gas in a downhole environment, comprising:
a mid-infrared light emitting diode;
a compartment for containing a reference gas sample;
detection means for detecting respective infrared signals transmitted on first and second optical paths extending from the diode, the apparatus being arranged such that in use the first optical path traverses a downhole gas sample and the second optical path traverses said compartment;
a processor for determining the concentration of a component of the downhole gas sample from the detected signals;
wherein the sensor is arranged such that, in use, the first optical path is substantially free of water and hydrocarbon in their liquid states.

18. A sensor according to claim 17, wherein the light emitting diode has a room temperature peak emission wavelength in the range from 3 to 5 $\mu$m.

19. A sensor according to claim 17, wherein the detection means is arranged to detect a further infrared signal transmitted on a third optical path extending from the light emitting diode, the third optical path having a defined mid-infrared absorbance at the emission wavelength of the diode.

20. A sensor according to claim 19, wherein the defined absorbance is zero.

21. A sensor according to claim 17, wherein the length of the first optical path is adjustable or selectable according to the expected concentration of said component.

22. A sensor according to claim 17, further comprising a filter for filtering the downhole gas sample to substantially remove liquids therefrom.

23. A sensor according to claim 17, comprising a plurality of mid-infrared light emitting diodes, each diode being adapted for use in a respective temperature range, and the diodes being selectively operable according to the downhole temperature.

24. A sensor according to claim 17, further comprising:
at least one optical window on the first optical path, the window defining a boundary of the downhole gas sample; and
an ultrasonic cleaner for removing liquid from the surface of the or each window.

25. A sensor according to claim 17, further comprising a waveguide which passes through the downhole gas sample, the infrared signal on the first optical path being transmitted along the waveguide by internal reflection.

26. A sensor according to claim 25, further comprising an ultrasonic cleaner for removing liquid from the surface of the waveguide.

27. A sensor according to claim 17, wherein the detection means comprises a plurality of respective photodiode detectors for detecting the transmitted infrared signals.

28. A sensor according to claim 17 which is located downhole.

29. A well tool comprising the sensor of claim 17.

30. A well tool according to claim 29 which is a production logging tool.

31. A well tool according to claim 29 which is a wireline sampling tool.

32. A sensor according to claim 17, further comprising a gas extraction membrane for extracting the downhole gas sample and substantially removing liquids therefrom, the membrane allowing the transport of gases across it but preventing the transport of liquid water and hydrocarbon.

* * * * *